United States Patent [19]

Gries et al.

[11] Patent Number: 5,210,290

[45] Date of Patent: May 11, 1993

[54] FLUOROBENZENESULFONAMIDES

[75] Inventors: Heinz Gries; Ulrich Niedballa; Hanns-Joachim Weinmann; Hans Bauer, all of Berlin, Fed. Rep. of Germany

[73] Assignee: Schering Aktiengesellschaft, Berlin and Bergkamen, Fed. Rep. of Germany

[21] Appl. No.: 667,309

[22] Filed: Mar. 12, 1991

[30] Foreign Application Priority Data

Mar. 12, 1990 [DE] Fed. Rep. of Germany ....... 4008179

[51] Int. Cl.$^5$ ............... C07C 317/48; C07C 317/26; C07C 317/28
[52] U.S. Cl. .................................. 562/430; 562/44
[58] Field of Search ................ 562/430, 44; 514/562

[56] References Cited

U.S. PATENT DOCUMENTS

| | | | |
|---|---|---|---|
| 3,558,698 | 1/1971 | Harrington et al. | 564/97 |
| 3,663,708 | 5/1972 | Harrington et al. | 514/485 |
| 3,920,444 | 11/1975 | Harrington et al. | 71/103 |
| 4,619,944 | 10/1986 | Youssefyeh et al. | 562/430 |
| 4,766,243 | 8/1988 | Fifolt | 424/9 |
| 4,804,529 | 2/1989 | Bardy et al. | 424/9 |
| 4,839,449 | 8/1989 | Mattes | 564/414 |

OTHER PUBLICATIONS

Blaszkiewicz et al., Chemical Abstracts 114(13):121756g (1990).
Trepka et al., *Journal of Agricultural and Food Chemistry*, 22(6), pp. 1111–1119 (1974).

*Primary Examiner*—Jos Dees
*Assistant Examiner*—B. Frazier
*Attorney, Agent, or Firm*—Millen, White, Zelano & Branigan

[57] ABSTRACT

Fluorobenzenensulfonamides of Formula I

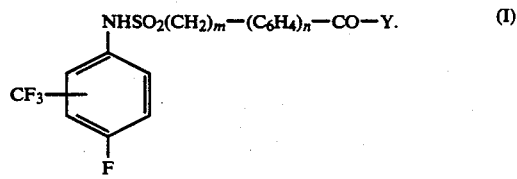

wherein
 m means the number 0, 1, 2, 3, or 4,
 n means the number 0 or 1, and
 Y means the residue of an aminocarboxylic or aminosulfonic acid,
with the proviso that m and n are not to stand simultaneously for the number 0 and, if desired, the acid groups are present in the form of their amides or in the form of salts with organic or inorganic bases, are suitable for use as NMR diagnostic aids.

15 Claims, No Drawings

FLUOROBENZENESULFONAMIDES

SUMMARY OF THE INVENTION

The invention relates to fluorobenzenesulfonamides, their use as NMR diagnostic aids, diagnostic media containing these fluorobenzenesulfonamides, as well as processes for the production of these compounds and media.

Modern medical technology has made it possible to provide images of extremely small morphological structures with a resolution coming close to that of tissue sections from anatomical textbooks.

Yet, information regarding the metabolic-physiological condition of tissue of the living organism cannot be obtained even with the aid of ultrasonic diagnostics, X-ray diagnostics, nuclear medicine, and even by means of NMR tomography. However, this knowledge is of considerable importance for a more accurate diagnosis and, in particular, for the planning and monitoring of a therapy, since optimum therapy can be successful only if a prediction regarding its effect can be made at an early point in time.

One important parameter of metabolic-physiological activity is the pH value. Many pathological processes entail a change in the hydrogen ion concentration. One of the most well-known examples is the release of lactic acid due to inadequate oxygen supply and the resultant anaerobic metabolizing of glucose. An anaerobic glycolysis takes place practically in all those cases where sufficient oxygen supply is no longer ensured. A short-term acidification can be detected, for example, in ranges of highest muscle activity. However, in this instance, the resultant lactic acid is relatively quickly transported away in the resting pause so that no hyperacidity can be found in the resting muscle. Conditions are different, though, in areas of permanent oxygen deficiency. In ischemic areas (infarction), a shift in pH value occurs on account of the increased anaerobic glycolysis. Similar effects can be observed in rapidly growing neoplasm. Besides the presence of a regulatory disturbance, oxygen deficiency exists in the area of a tumor so that here again acidification occurs by the anaerobic metabolizing of carbohydrates.

Accordingly, the determination of the tissue pH value leads to important information on the function, condition, and growth of the cells so that it is desirable, for example, to localize metabolic acidoses. (Am. J. Physiol. 246 : R 409, 1984; R. Nuccitelli, D. W. Deamer, Eds. 1982 Intracellular pH: Its Measurement, Regulation and Utilization in Cellular Functions, Liss, New York.) Besides measuring the pH value with pH electrodes, NMR spectroscopy has also been utilized recently for this purpose. It has become possible for the first time with the aid of this procedure to determine the pH value of the tissue non-invasively.

Determination of the pH value with the aid of NMR spectroscopy is based on the measurement of the signals from a chemical compound which is in a pH-dependent, reversible equilibrium. If this equilibrium is slow with respect to the NMR time scale, then the signals of all components can be obtained, and the signal intensities correspond to the concentrations of the equilibrium components. In contrast thereto, with a fast equilibrium, only one signal can be measured, and the chemical shift is given by the chemical displacement of the equilibrium components and their concentration.

In a two-component equilibrium, with knowledge of the $pK_a$ value and the chemical shift of the components, it is then possible to calculate the pH value with the aid of the Henderson-Hasselbalch equation.

The following table demonstrates which atomic nuclei are suitable, in principle, for NMR imaging or spectroscopy, respectively:

| Nucleus | Frequency at 1 tesla MHz | Rel. Measuring Sensitivity $^1H = 1$ | Concentration in Biol. Tissue | Chemical Shift | Chemical Modification Possibility | $T^1$ Relaxation Times |
|---|---|---|---|---|---|---|
| $^1H$ | 42.6 | 1.0 | 100 mol/l | Small | Very High | 0.1-3 sec. |
| $^{19}F$ | 40.1 | 0.8 | <<1 mmol/l | Very Large | Very High | 1-5 sec. |
| $^{23}Na$ | 11.3 | 0.09 | 100 mmol/l | — | Practically Zero | <0.1 sec. |
| $^{31}P$ | 17.2 | 0.06 | 10 mmol/l | Medium | Limited | 1-5 sec. |
| $^{13}C$ | 10.7 | 0.0002 | 1 mmol/l | Very Large | Very High | 1-10 sec. |

The $^{31}p$ nucleus has been utilized for 15 years as a noninvasive measuring probe for intracellular pH value measurement (j. Biol. Chem. 248 : 7276, 1973). the pH-sensitive signal here is the signal from the inorganic phosphate of the equilibrium of hydrogen phosphate - dihydrogen phosphate; the $^{31}p$ signal of phosphocreatine serves as the reference.

However, use of the $^{31}p$ nucleus for determination of the pH value also has its limits: Thus, an exact determination of the pH value in a well localized tissue volume in human subjects is impossible even with the utilization of 2T NMR tomographs. This is due to the relatively low phosphate concentrations as well as to the fact that the $^{31}p$ signal is difficult to detect from the viewpoint of measuring technique. Spurious signals in the range of inorganic phosphate, heterodyning of the inorganic P signal by other P metabolites, or the lack of a reference signal can prevent a pH measurement. Additional difficulties reside in the low sensitivity of the nucleus and the low pH dependency of the chemical shift. The accuracy of the pH measurement is affected above all by the determination of the chemical shifts of the signals and is no better than 0.2 pH units. Furthermore, resonant signals can be entirely missing when using endogenous phosphates because the compounds are accumulated only in such low concentrations (for example in the intestine or in Ehrlich ascites tumor cells) that pH value determination is impossible.

Based on these facts, only a rather inexact pH determination is possible in comparatively large volumes. For producing a satisfactory $^{31}p$ spectrum, signals are picked up from the measuring volume of about 100 cc with an accumulation period of 15 minutes.

When using nuclei other than $^{31}P$, the $^{19}$fluorine nucleus is the nucleus of choice since it yields a readily measurable NMR signal very similar to that of the hydrogen proton (just as $^1H$, it has a nuclear spin of ½), i.e. the same receiver and transmitter coils can be used as in $^1H$ NMR diagnostics, it has a high sensitivity (about 83% of $^1H$), is present in 100% frequency distribution, and the signals are distributed over a large frequency range. Additional advantages that can be cited are the absence of fluorine in the organism (except for the teeth) so that no complications can arise with endogenous F signals (lack of a $^{19}F$ background signal), as well as the favorable chemical accessibility.

Information obtainable by way of using F molecules in NMR diagnostics cannot be obtained by any other diagnostic imaging or quasi-imaging procedure: the signal can change greatly in the body—depending on the chemical condition—thus permitting the quantifying of biochemical reactions and making it possible to directly observe physiological processes. In spite of these seductive properties, it must be pointed out that the concentration is problematic. A meaningful experiment requires $^{19}F$ concentrations of $>1$ mmol F/l, i.e., the compounds to be administered must exhibit excellent compatibility and must show good solubility in water so that solutions of high concentrations in the minimally smallest volumes can be used.

The frequency (chemical shift) of a fluorine line is determined by the position of the F atom in the molecule. This also holds true, in principle, for all other atomic nuclei, but the chemical shift is especially strongly pronounced in case of the fluorine atom. In order to observe and/or quantify a shift of the fluorine signal, a related (reference) line is needed. This frequency line can be the $^1H$ signal, an external F standard or, respectively, an unchanging F line which is likewise within the area to be measured. This reference line can be present in another molecule having a similar distribution or, preferably, in the molecule proper that is used as the indicator. The most favorable situation exists in the last-mentioned case since here only one compound is administered, and there are no problems whatever with susceptibility effects so that an indubitable correlation of the signals is possible.

Consequently, there is a need for finding suitable compounds reacting to a change in the pH value with an altered measured value (resonant frequency) in the NMR spectrum with the simultaneous presence of a reference line. Furthermore, these compounds and, respectively, the diagnostic media containing these compounds must exhibit the following properties:

(a) a large chemical shift per pH unit;
(b) suitable pK values for in vivo measurements;
(c) pharmacokinetics suitable for diagnostics;
(d) accumulation in the target organs adequately high for a measurement;
(e) good compatibility and low toxicity;
(f) metabolic stability;
(g) high chemical stability and shelf life;
(h) good water solubility.

The compounds described heretofore (and only for in vitro investigation!) (Annals of the New York Academy of Science, S. M. Cohen, Ed. 1987, 508:33) do not meet these requirements. For example, they cannot yield a more accurate pH determination than with $^{31}P$ since the pH dependency of the chemical shift is too low ($\leq 1$ ppm/pH) and/or their pH values lie outside of the physiological range an/or their resonant frequencies are dependent not only on the pH but also on the field strength. Also, the disclosed compounds, due to their poor compatibility, are unsuitable for use in animal experiments or even in clinical trials.

SUMMARY OF THE INVENTION this invention provides compounds and media exhibiting these useful properties, as well as processes for their production.

Upon further study of the specification and appended claims, further objects and advantages of this invention will become apparent to those skilled in the art.

It has been found that fluorobenzenesulfonamides of Formula I

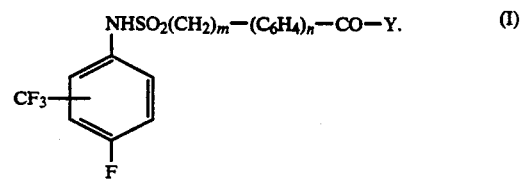

wherein
m means the number 0, 1, 2, 3 or 4,
n means the number 0 or 1, and
Y means the residue of an aminocarboxylic or aminosulfonic acid,
with the proviso that m and n are not to stand simultaneously for the number 0 and, if desired, the acid groups are present in the form of their amides or in the form of salts with organic or inorganic bases,
are surprisingly excellently suited for the production of NMR diagnostic aids.

If the compounds according to this invention contain more than one acid group in the molecule, then all (compare Example 10), as well as only one (compare Example 55) of the acid groups can be present in the form of their amides or salts.

Suitable as the aminocarboxylic and aminosulfonic acids (or their amides) are their natural as well as synthetic representatives.

Suitable aminocarboxylic and aminosulfonic acid substituents Y are those wherein the nitrogen atom forms an amide bond with the carbonyl group of the compound of formula I, and include groups having 1 to 30 carbon atoms, 1 to 4 acid groups, and having a molecular weight range of preferably less than 1000 daltons. There may be one or two substituent groups attached to the amide nitrogen atom. Suitable groups for the radical between the nitrogen atom and the carboxylic or sulfonic acid moities include one or more linear or branched alkyl groups of 1 to 10 carbon atoms, or $C_{7-10}$-alkaryl or -aralkyl, any of which are optionally substituted by 1 to 4 OH or COOH groups.

These aminocarboxylic and aminosulfonic groups function to increase the solubility and tolerability of the compounds. Residues Y that can be cited as examples include:

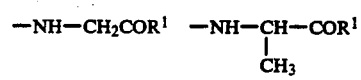

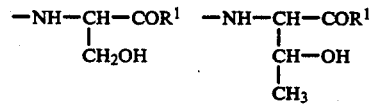

-continued

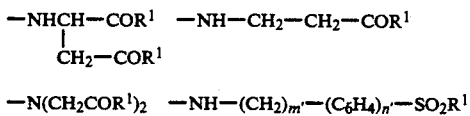

wherein
R¹ means a hydroxy group or a

residue,
 wherein
  R² and R³, independently of each other, mean a hydrogen atom, a linear or branched, saturated or unsaturated alkyl group of 1–16 carbon atoms, optionally substituted by 1–5 hydroxy or $C_1$–$C_4$-alkoxy groups, or a $C_{4-6}$-aryl or $C_{7-10}$-aralkyl group, or R² and R³ jointly with the nitrogen mean a saturated or unsaturated $C_{3-5}$ five- or six-membered ring optionally containing a further nitrogen, oxygen, sulfur atom or a carbonyl group, and
  m' and n' each independently have the same definition as m and n above.

Suitable alkyl substituents R² and R³ are saturated, unsaturated, straight- or branched-chain or cyclic hydrocarbons of up to 16 carbon atoms, preferably saturated hydrocarbons of up to 7 carbon atoms which are substituted, if desired, by 1–5 hydroxy or lower alkoxy groups.

Lower alkoxy groups are to contain in each case 1–4 carbon atoms and are to comprise, in particular, methoxy and ethoxy groups.

Examples of optionally substituted alkyl groups are the methyl, ethyl, hydroxymethyl, 1-hydroxyethyl, 2-hydroxyethyl, 2-hydroxy-1-(hydroxymethyl)ethyl, 1-(hydroxymethyl)ethyl, propyl, isopropyl, propenyl, isopropenyl, 2-, and 3-hydroxypropyl, 2,3-dihydroxypropyl, butyl, isobutenyl, 2-, 3-, and 4-hydroxybutyl, 2-, 3-, and 4-hydroxy-2-methylbutyl, 2- and 3-hydroxyisobutyl, 2,3,4-trihydroxybutyl, cyclohexyl, pentyl, hexyl, bis- and tris(hydroxymethyl)methyl, 2,3-dihydroxy-1-(hydroxymethyl)propyl, 2,3,4,5,6-pentahydroxyhexyl, 1,3,4-trihydroxybutyl-2- and 2-methoxyethyl groups.

Unsubstituted alkyl groups of 1–7 carbon atoms are preferred, such as, for example, the methyl, ethyl, n-propyl, isopropyl, n-butyl, isobutyl, pentyl and hexyl groups. Furthermore preferred are mono- and polyhydroxy-substituted alkyl groups of 2–7 carbon atoms and 1–5, preferably 1–4 hydroxy groups, such as, for example, 2-, and 3-hydroxypropyl, 1,3-dihydroxyisopropyl, 1-(hydroxymethyl)ethyl, bis- and tris(hydroxymethyl)methyl, 2,3-dihydroxy-1-hydroxymethylpropyl, 2,3,4,5,6-pentahydroxyhexyl and preferably 2-hydroxyethyl, 2-hydroxy-1-(hydroxymethyl)ethyl, 2,3-dihydroxypropyl and 2,3,4-trihydroxybutyl.

In case R² or R³ means an aryl or aralkyl group, the phenyl and, respectively, benzyl group is preferred.

The heterocyclic 5- or 6-membered ring formed by R² and R³ with inclusion of the amide nitrogen can be saturated or unsaturated and can contain, if desired, a nitrogen, oxygen, sulfur atom or a carbonyl group.

Examples of suitable heterocycles that can be mentioned are: the pyrrolidinyl, piperidyl, pyrazolininyl, piperidonyl, pyrrolinyl, pyrazolinyl, piperazinyl, morpholinyl, imidazolidinyl, oxazolidinyl, thiazolidinyl rings.

The —CO—Y— and —$SO_2R^1$ substituent is preferably in the o- or p-position of the benzene ring.

The acidic hydrogen atoms present in the compounds of general Formula I can optionally be replaced entirely or partially by cations of inorganic and/or organic bases or amino acids. Suitable inorganic cations are, for example, the lithium ion, the potassium ion, the calcium ion, the magnesium ion and especially the sodium ion. Suitable cations of organic bases are, inter alia, those of primary, secondary or tertiary amines, e.g. ethanolamine, diethanolamine, morpholine, glucamine, N,N-dimethylglucamine and especially N-methylglucamine. Suitable cations of amino acids are, for example, those of lysine, of arginine and of ornithine, as well as the amides of otherwise acidic or neutral amino acids.

The fluorobenzenesulfonamides of Formula I are produced in that, in a manner known per se, compounds of Formula II

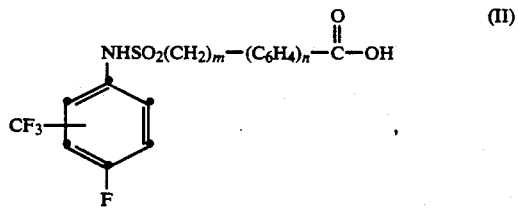

optionally in activated form
are reacted with compounds of Formula III

wherein
Y' means the residue of an optionally blocked aminocarboxylic or aminosulfonic acid, or the residue of an aminocarboxylic or aminosulfonic acid amide wherein any hydroxy groups that may be present are optionally blocked,
thereafter the blocking groups are removed, the acid groups are optionally converted into the corresponding salts with organic or inorganic bases, or optionally after activation of the acid groups contained in Y are reacted, if desired, with an amine of Formula IV

wherein
R²' and R³' have the meanings given for R² and R³, any hydroxy groups present therein being optionally blocked,
and any blocking groups that may be present are removed.

Suitable acids groups are lower alkyl, aryl and aralkyl groups, e.g. the methyl, ethyl, propyl, n-butyl, tert-butyl, phenyl, benzyl, diphenylmethyl, triphenylmethyl, bis(p-nitrophenyl)methyl groups, as well as trialkylsilyl groups.

The acids can also be utilized in the form of their salts, preferably as the ammonium salt.

The acid blocking groups are split off in accordance with methods known to one skilled in the art, for example by hydrolysis, hydrogenolysis, alkaline saponification of the esters with alkali in an aqueous-alcoholic solution at temperatures of 0°-50° C., acidic saponification with mineral acids, or, in the case of tert-butyl esters, for example, with the aid of trifluoroacetic acid.

Suitable hydroxy blocking groups are all those which can be easily introduced and can also again be readily split off thereafter with restoration of the finally desired free hydroxy group. Preferred blocking groups are ether groups, such as, for example, the benzyl, 4-methoxybenyl, 4-nitrobenzyl, trityl, di- and triphenylmethyl, trimethylsilyl, dimethyl-tert-butylsilyl, diphenyl-tert-butylsilyl groups.

The hydroxy groups can also be present, for example, as THP ethers, α-alkoxyethyl ethers, MEM ethers, or as esters with aromatic or aliphatic carboxylic acids, such as, for example, acetic acid or benzoic acid. In case of polyols, the hydroxy groups can also be blocked in the form of ketals with, for example, acetone, acetaldehyde, cyclohexanone or benzaldehyde.

The hydroxy blocking groups are split off conventionally, for example in case of a benzyl ether by reductive cleavage with lithium/ammonia or by hydrogenolytic cleavage in the presence of, for example, palladium-carbon, in case of an ester, for example, by alkaline saponification in aqueous-alcoholic solution at temperatures of 0°-50° C. and, respectively, in case of tert-butyl esters with the aid of trifluoroacetic acid as well as, in case of an ether or ketal cleavage, by acid treatment with the aid of, for example, cation exchangers, trifluoroacetic acid, or mineral acids (see, for example, "Protective Groups in Organic Synthesis", T. W. Greene, John Wiley and Sons 1981).

Examples of an activated carboxyl group are anhydride, p-nitrophenyl ester and acid chloride.

The reaction of the carboxylic acids of Formula II with the compounds of Formula III H-Y' and, respectively, of the thus-obtained fluorobenzenesulfonamides of Formula I wherein Y means the residue of an aminocarboxylic or aminosulfonic acid with amines of Formula IV HNR$^2$'R$^3$', takes place according to methods known from the literature, e.g. in the presence of reagents such as carboniimide, preferably dicyclohexylcarbodiimide (DCC) (for example, Am. Soc. 81 : 890) in aprotic solvents, such as, for example, dimethylformamide, dioxane, dichloromethane or their mixtures at temperatures of −10° C. to 100° C., preferably −10° C. to room temperature, within 1-24, preferably 2-12 hours.

Linkage of the amide bonds can also be effected by aminolysis of activated carboxyl groups with compounds of general Formula III or IV, respectively.

Thus, the aminolysis of, for example, esters takes place in the liquid phase, e.g. in a suitable higher-boiling solvent, such as dimethylformamide, dimethylacetamide, or dimethyl sulfoxide. The reaction temperatures range at about 20° C.-200° C., temperatures of 100° C.-180° C. being preferred. The reaction times are between 2 hours and 2 days, reaction periods of between 4 hours and 36 hours being preferred.

Moreover, all of the methods known to one skilled in the art for converting carboxy groups into amide groups can be utilized for the synthesis of the fluorobenzenesulfonamides of Formula I according to this invention, thus, for example, the method according to Krejcarek and Tucker, Biochem. Biophys. Res. Commun. 77 : 581 (1977) by way of mixed anhydrides.

Suitable amines of Formula IV that can be cited are, for example: dimethylamine, diethylamine, di-n-propylamine, diisopropylamine, di-n-butylamine, diisobutylamine, di-sec-butylamine, N-methyl-n-propylamine, dioctylamine, dicyclohexylamine, N-ethylcyclohexylamine, diisopropenylamine, benzylamine, aniline, 4-methoxyaniline, 4-dimethylaminoaniline, 3,5-dimethoxyaniline, morpholine, pyrrolidine, piperidine, N-methylpiperazine, N-ethylpiperazine, N-(2-hydroxyethyl)piperazine, N-(hydroxymethyl)piperazine, piperazinoacetic acid isopropylamide, N-(piperazinomethylcarbonyl)morpholine, N-(piperazinomethylcarbonyl)pyrrolidine, 2-(2-hydroxymethyl)piperidine, 4-(2-hydroxyethyl)piperidine, 2-hydroxymethylpiperidine, 4-hydroxymethylpiperidine, 2-hydroxymethylpyrrolidine, 3-hydroxypiperidine, 4-hydroxypiperidine, 3-hydroxypyrrolidine, 4-piperidone, 3-pyrroline, piperidine-3-carboxylic acid amide, piperidine-4-carboxylic acid amide, piperidine-3-carboxylic acid diethylamide, piperidine-4-carboxylic acid dimethylamide, 2,6-dimethylpiperidine, 2,6-dimethylmorpholine, N-acetylpiperazine, N-(2-hydroxypropionyl)piperazine, N-(3-hydroxypropionyl)piperazine, N-(methoxyacetyl)piperazine, 4-(N-acetyl-N-methylamino)piperidine, piperidine-4-carboxylic acid (3-oxapentamethylene)amide, piperidine-3-carboxylic acid (3-oxapentamethylene)amide, N-(N',N'-dimethylcarbamoyl)piperazine, pyrazoline, pyrazolidine, imidazoline, oxazolidine, thiazolidine, 2,3-dihydroxypropylamine, N-methyl-2,3-dihydroxypropylamine, 2-hydroxy-1-(hydroxymethyl)ethylamine, N,N-bis(2-hydroxyethyl)amine, N-methyl-2,3,4,5,6-pentahydroxyhexylamine, 6-amino-2,2dimethyl-1,3-dioxepin-5-ol, 2-hydroxyethylamine, 2-amino-1,3-propanediol, diethanolamine, ethanolamine.

The polyhydroxyalkylamines can advantageously also be utilized for the reaction in blocked form, for example as O-acyl derivatives or as ketals. This holds true, in particular, if these derivatives can be prepared more conveniently and more economically than the polyhydroxyalkylamines proper. A typical example is 2-amino-1-(2,2-dimethyl-1,3-dioxolan-4-yl)ethanol, the acetonide of 1-amino-2,3,4-trihydroxybutane, prepared according to DOS 3,150,917.

The subsequent removal of the blocking groups is without problems and can be accomplished, for example, by treatment with an acidic ion exchanger in an aqueous-ethanolic solution.

The synthesis of the educts of Formula II takes place in a manner known per se (Houben-Wey), "Methoden der organischen Chemie" vol. IX, pp. 343, 398, 547 and 557, Georg Thieme Publishers, Stuttgart, 1955) by reaction of 4-fluoro-2-trifluoromethylaniline or 4-fluoro-3-trifluoromethylaniline with halosulfonyl derivatives (e.g. chlorosulfonylacetic acid ester of chlorosulfonylbenzoic acid) in the presence of acid captors, such as, for example, tertiary amine [e.g. triethylamine, pyridine, N,N-dimethylaminopyridine, 1,5-diazabicyclo[4.3.0]nonene-5(DBN), 1,5-diazabicyclo[5.4.0]undecene-5 (DBU)], alkali, alkaline earth carbonate or bicarbonate (e.g. sodium, magnesium, calcium, barium, potassium carbonate and bicarbonate) in solvents such as, for example, dioxane, dichloroethane or dichloromethane at temperatures of between −20° C. to +50° C., preferable −5°-20° C.

The saponification of esters obtained in this way, which is to be optionally performed takes place according to methods known from the literature. As has been mentioned above, however, the esters can likewise serve as the starting materials for the subsequent reactions.

After preparation of the desired compound of Formula I, any acidic hydrogen atoms present in the molecule can be substituted by cations of inorganic and/or organic bases.

In this case, neutralization is effected with the aid of inorganic bases (e.g. hydroxides, carbonates or bicarbonates) of, for example, sodium potassium, lithium, magnesium and calcium and/or organic bases, such as, inter alia, primary, secondary and tertiary amines, e.g. ethanolamine, morpholine, glucamine, N-methyl- and N,N-dimethylglucamine.

For producing the neutral salts, it is possible, for example, to add an equivalent of the desired bases to the acids in an aqueous solution or suspension. The resultant solution can thereafter be concentrated to dryness under vacuum or freeze-dried. It is frequently advantageous to precipitate the thus-formed neutral salts by adding water-miscible solvents, such as, for example, lower alcohols (metahnol, ethanol, isopropanol, and others), lower ketones (acetone and others), polar ethers (tetrahydrofuran, dioxane, 1,2-dimethoxyethane and others), thus obtaining crystallized products which can be easily isolated and thoroughly purified.

In case the acidic compounds contain several free acid groups, then it is often expedient to produce neutral mixed salts containing inorganic as well as organic cations as the counterions.

The diagnostic media of this invention can be prepared likewise in a manner known per se by suspending or dissolving the compounds according to the invention—optionally with addition of the additives customary in galenic pharmacy—in an aqueous medium and then optionally sterilizing the suspension or solution. Suitable additives are, for example, physiologically acceptable buffers (e.g. tromethamine), small additions of complexing agents (such as, for example, diethylenetriaminepentaacetic acid) or, if required, electrolytes, e.g. sodium chloride or, if necessary, antioxidants, e.g. ascorbic acid.

In case suspensions or solutions of the media of this invention in water or physiological saline solution are desirable for enteral administration or other purposes, then the media are mixed with one or several of the adjuvants customary in galenic pharmacy (e.g. methylcellulose, lactose, mannitol) and/or tensides (e.g. lecithins, "Tween", "Myrj") and/or flavoring materials to improve taste (e.g. ethereal oils).

The fluorine-containing compounds according to this invention can be utilized with advantage in in vivo NMR diagnostics, i.e. for NMR imaging and in NMR spectroscopy as an indicator of various parameters. Thus, it is possible, inter alia, to measure, with the aid of locally resolved spectroscopy and thus in a tissue-specific fashion, the pH, $pO_2$, $pCO_2$, temperature, redox processes and reaction kinetics.

It has furthermore been found that the compounds of this invention are surprisingly distinguished by a very good tolerability.

The pharmaceutical agents of this invention are preferably produced in a concentration of 1µmol-1 mol/l. They are normally administered in doses amounting to 0.005-20 mmol/kg body weight, preferably 0.05-5 mmol/kg body weight. They are intended for enteral and parenteral administration.

The media of this invention meet the variegated requirements for being suitable as diagnostic aids for NMR tomography and spectroscopy. Furthermore, they exhibit the high efficacy required to introduce into the body a minimum amount of burdening foreign substances, and the good tolerability needed for maintaining the noninvasive character of the examinations.

The good water solubility of the media of this invention makes it possible to prepare highly concentrated solutions, thus maintaining the volume load on the circulation within tolerable limits and compensating for dilution by body fluid, i.e. NMR diagnostic acids must exhibit 100-1,000 times the water solubility of media utilized in in vitro NMR spectroscopy.

The good tolerability of the compounds according to this invention permits the study and NMR spectroscopical measurement of the pH value in the living organism. In this connection, an administration of 10 µmol/kg to 10 mmol/kg body weight permits a determination, without problems, of the change in chemical shift of the $^{19}F$ signal as related to the reference signal (e.g. an intramolecular $CF_3$ group) and thus of the pH value. The administered solution is quickly distributed in the organism and consequently is capable of detecting regions of differing pH value. Moreover, by means of an appropriate dosage, it is possible to bring about a change in pH and thus optionally a therapeutic effect.

In order to be able to detect small changes in pH value, the compounds having a pK value in the proximity of the biological or pathological pH value of the tissue of interest are advantageous. Normally those compounds are of special interest which have a pK value of between 2 and 9, preferably between 6 and 8. Compounds detecting the pH value of the gastrointestinal tract advantageously exhibit a pK of between 2 and 8. Since the maximum accuracy of the pH determination is present in the range of maximum change of the chemical shift per unit, i.e. at the pK value of the respective compound, a very good analysis of biological processes is made possible. Thus, the pH of blood is about 7.2-7.4; pathological regions can have an altered pH value which can drop, for example, down to 4.0 or lower.

Compounds with a pK value of between 5 and 7 are advantageous for imaging the kidney function and/or for analysis of the primary and secondary urine, since the pH value of urine is normally below that of blood. For determining the intragastral pH value, those compounds are advantageous which show most clearly a change in chemical shift between ph 2 and 6, since the pH value of gastric fluid can strongly fluctuate between almost 1 and 7.

Accordingly, by the use of the very well tolerated, novel fluorinated measuring probes, it has become possible to perform, in relatively small volumes (e.g. 10 cc), locally resolved spectroscopy, and to determine physiologically significant parameters, such as, for example, the pH value, precisely in a short measuring time without interference and, respectively, superposition by other molecules.

For in vivo imaging (NMR imaging), the aforementioned compounds likewise show suitability. In this case, the resultant image not only shows information on the altered chemical shift, but also includes the local concentrations of the fluorinated compounds by means of the scanning sequences customary in MRt in one imaging step. The advantage $^{19}F$ imaging as compared with $^{1}H$ tomography resides in that the distribution of the pharmaceutical medium can be depicted directly without superposition by interfering structures.

Thus, if is possible, for example, to provide an excellent contrasting of the renal elimination system (kidneys, urether, bladder) upon intravenous administration of the compounds according to this invention, provided in a dose of 5 μmol/kg to 20 mmol/kg preferably 0.1 mmol/kg to 5 mmol/kg. In this connection, it has also been discovered surprisingly that the additional injection of a paramagnetic compound (e.g., GdDTPA/-dimeglumine) in a dose of 1 μmol/kg to 2 mmol/kg, preferably 50 μmol/kg to 500 μmol/kg, leads to a marked improvement in image quality.

When coupled to macromolecules, e.g., monoclonal antibodies, the compounds of this invention can also be utilized as organ- and tumor-specific therapeutic agents and diagnostic media.

If the $^{18}F$ isotope is contained in the compounds of this invention, then the compounds are suited for diagnostic media for positron emission tomography (PET). PET, using the present compounds, can be performed analogously to known procedures, e.g., those in Diagnostic Imaging 7, (11) 138 (1985).

The compounds of Formula I according to this invention are likewise usable against all bacterial infections to be treated chemotherapeutically with sulfonamides.

The examples set forth below serve for a more detailed description of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 40 08 179.6, filed Mar. 12, 1990, are hereby incorporated by reference.

In the following examples, "calcd" means calculated.

EXAMPLE 1

2-[2l-[N-(4-Fluoro-2-trifluoromethylphenyl)sulfamoyl]-acetylamino]acetic Acid (a)

2-[2l-[N-(4-Fluoro-2-trifluoromethylphenyl)sulfamoyl]-acetylamino]acetic Acid Ethyl Ester 1.561 g (5 mmol) of 2-[2l-[N-(4-fluoro-2-trifluoromethylphenyl)sulfamoyl]-acetylamino]acetic acid, 700 mg (5 mmol) of glycine ethyl ester hydrochloride, and 766 mg (5 mmol) of hydroxybenzotriazole, hydrate, are introduced into 100 ml of dimethylformamide and cooled under agitation to −12° C. Then 506 mg (5 mmol) of triethylamine is added thereto, the mixture is stirred for 10 minutes, and combined with 1.03 g (5 mmol) of dicyclohexylcarbodiimide. The mixture is allowed to thaw and stirred overnight. The solid matter is suctioned off and the mixture is concentrated to dryness under vacuum. The residue is distributed between water and dichloromethane. The organic solution is dried over sodium sulfate and concentrated to dryness under vacuum. The residue is crystallized from ethanol.

Yield: 1.932 g (77.7% of theory)
Melting point: 128°–130° C.
Analysis: $C_{13}H_{14}F_4N_2O_5S$ (386.32):
C,40.42; H,3.65; F,19.67; N,7.25; O,20.71; S,8.30:Calcd.
C,40.71; H,3.61; F,19.54; N,7.83; O,—; S,8.21:Found.

(b)

2-[2-[N-(4-Fluoro-2-trifluoromethylphenyl)sulfamoyl]-acetylamino]acetic Acid 1.30 g (3.37 mmol) of the ethyl ester prepared according to Example 1(a) is dissolved in 25 ml of warm ethanol and combined with 5 ml (10 mmol) of 2N sodium hydroxide solution. The mixture is heated under stirring until no starting material can be detected any more, acidified with hydrochloric acid to a pH of 3, and concentrated under vacuum to dryness. The compound is taken up in ethyl acetate and also crystallized therefrom.

Yield: 960 mg (79.6% of theory)
Melting point: 168°–170° C.
Analysis: $C_{11}H_{10}F_4N_2O_5S$ (358.27):
C,36.88; H,2.81; F,21.21; N,7.82; O,22.33; S,8.95:Calcd.
C,37.05; H,2.96; F,21.09; N,7.76; O,—; S,8.84:Found.

EXAMPLE 2

2-[2-[N-(4-Fluoro-3-trifluoromethylphenyl)sulfamoyl]-acetylamino]acetic Acid (a)

2-[2-[N-(4-Fluoro-3-trifluoromethylphenyl)sulfamoyl]-acetylamino]acetic Acid Ethyl Ester Under nitrogen, 1.81 g (6 mmol) of 2-[2-[N-(4-fluoro-3-trifluoromethylphenyl)sulfamoyl]acetic acid, 0.845 g (6 mmol) of glycine ethyl ester hydrochloride (98%), and 0.919 g (6 mmol) of hydroxybenzotriazole, hydrate, are added to 100 ml of dimethylformamide and the mixture is cooled to −10° C. under agitation. Then 0.607 g (6 mmol) of triethylamine is added thereto, the mixture is agitated for 10 minutes and combined with 1.24 g (6 mmol) of dicyclohexylcarbodiimide. The mixture is stirred for another hour at the low temperature and then overnight without cooling. The mixture is suctioned off from the solid matter, the solution is concentrated to dryness under vacuum, and the residue is distributed between sodium bicarbonate solution and ethyl acetate. The ethyl acetate solution is washed with water, dried over sodium sulfate, and concentrated to dryness under vacuum. The residue is crystallized from ethyl acetate/hexane, thus obtaining 1.72 g (74.1% of theory) of the title compound.

Melting point: 145°–147° C.
Analysis: $C_{13}H_{14}F_4N_2O_5S$ (386.32):
C,40.42; H,3.66; F,19.67; N,7.25; O,20.71; S,8.30:Calcd.
C,40.46; H,3.78; F,19.57; N,7.34; O,—; S,8.37:Found.

(b)

2-[2-[N-(4-Fluoro-3-trifluoromethylphenyl)sulfamoyl]-acetylamino]acetic Acid 1.66 g (4.30 mmol) of the compound prepared in Example 2(a) is dissolved in 20 ml of dioxane. The mixture is combined with 5.4 ml (10.8 mmol) of 2N sodium hydroxide solution, warmed on a water bath until no starting material can be detected any longer, and then adjusted to pH 3 with hydrochloric acid. The solution is concentrated to dryness under vacuum, the residue is distributed between ethyl acetate and water. The ethyl acetate solution is dried over sodium sulfate and concentrated to dryness under vacuum. The title compound is crystallized from ethyl acetate/hexane.

Yield: 1.271 mg (82.50% of theory)
Melting point: 146°–148° C.
Analysis: $C_{11}H_{10}F_4N_2O_5S$ (358.26):
C,36.88; H,2.81; F,21.21; N,7.82; O,22.33; S,8.95:Calcd.
C,36.82; H,3.01; F,21.01; N,7.78; O,—; S,8.83:Found.

EXAMPLE 3

2-[2-[N-(4-Fluoro-2-trifluoromethylphenyl)sulfamoyl]-acetylamino]-2-hydroxymethylacetic Acid (a)

2-[2-[N-(4-Fluoro-2-trifluoromethylphenyl)sulfamoyl]acetylamino]-2-hydroxymethylacetic Acid Methyl Ester Under the conditions of Example 2(a), 3.29 g (10.93 mmol) of 2-[N-(4-fluoro-2-trifluoromethylphenyl)sulfamoyl]acetic acid, 1.70 g (10.93 mmol) L-serine methyl ester hydrochloride, 1.67 g (10.93 mmol) of hydroxybenzotriazole, hydrate, as well as 1.11 g (10.93 mmol) of triethylamine and 2.26 g (10.93 mmol) of dicyclohexylcarbodiimide are reacted and worked up analogously. The crude product is chromatographed on silica gel. The title compound is eluted with ethanol and crystallized upon concentration.

Yield: 3.44 mg (78.2% of theory)
Melting point: 143°–145° C.
Analysis: $C_{13}H_{14}F_4N_2O_6S$ (402.32):
C,38.81; H,3.51; F,18.89; N,6.96; O,23.86; S,7.97:Calcd.
C,39.00; H,3.45; F,18.80; N,6.92; O,—; S,8.07:Found.

(b)

2-[2-[N-(4-Fluoro-2-trifluoromethylphenyl)sulfamoyl]acetylamino]-2-hydroxymethylacetic Acid Under the conditions of Example 2(b), 1.91 g (4.75 mmol) of the ester prepared in Example 3(a) is saponified with 5.94 ml (11.88 mmol) of 2N sodium hydroxide solution in 2- ml of dioxane. After performing an analogous working-up operation, a solid is obtained which is recrystallized from ethyl acetate/hexane. The yield of title compound is 1.49 g (80.7% of theory).

Melting point: 145°–147° C.
Analysis: $C_{12}H_{12}F_4N_2O_6S$ (388.29):
C,37.12; H,3.12; F,19.57; N,7.21; O,24.72; S,8.26:Calcd.
C,37.02; H,3.16; F,19.75; N,7.19; O,—; S,8.42:Found.

EXAMPLE 4

2-[2-[N-(4-Fluoro-3-trifluoromethylphenyl)sulfamoyl]acetylamino]-2-hydroxymethylacetic Acid (a)

2-[2-[N-(4-Fluoro-3-trifluoromethylphenyl)sulfamoyl]acetylamino]-2-hydroxymethylacetic Acid Methyl Ester Under the conditions of Example 2(a), 3.29 g (10.93 mmol) of 2-[2-[N-(4-fluoro-2-trifluoromethylphenyl)sulfamoyl]acetic acid, 1.70 g (10.93 mmol) of L-serine methyl ester hydrochloride, 1.67 g (10.93 mmol) of hydroxybenzotriazole, hydrate, as well as 1.11 g (10.93 mmol) of triethylamine and 2.26 g (10.93 mmol) of dicyclohexylcarbodiimide are reacted and worked up analogously. The crude product is purified by column chromatography on silica gel.

The title compound is eluted with ethyl acetate.
Yield: 3.17 mg (72.1% of theory)
Analysis: $C_{13}H_{14}F_4N_2O_6S$ (402.32):
C,38.81; H,3.51; F,18.89; N,6.96; O,23.86; S,7.97:Calcd.
C,39.09; H,3.55; F,18.77; N,7.18; O,—; S,7.99:Found.

(b)

2-[2-[N-(4-Fluoro-3-trifluoromethylphenyl)sulfamoyl]acetylamino]-2-hydroxymethylacetic Acid 2.30 g (5.72 mmol) of the ester prepared in Example 4(a) is dissolved in 30 ml of dioxane and combined with 6 ml (12 mmol of 2N barium hydroxide solution. The mixture is stirred at room temperature for 24 hours (no more starting material is detectable), adjusted to pH 5 with hydrochloric acid, and concentrated to dryness under vacuum. The residue is distributed between ethyl acetate and acidified water. The ethyl acetate solution is dried over sodium sulfate and concentrated to dryness under vacuum, thus obtaining the tile compound as a material uniform per thin-layer chromatography. The yield is 1.613 g (72.6% of theory).

Analysis: $C_{12}H_{12}F_4N_2O_6S$ (388.29):
C,37.12; H,3.12; F,19.57; N,7.21; O,24.72; S,8.62:Calcd.
C,37.03; H,3.18; F,19.44; N,7.16; O,—; S,8.20:Found.

EXAMPLE 5

2-[2-[N-(4-Fluoro-3-trifluoromethylphenyl)sulfamoyl]-benzolamino]-2-hydroxymethylacetic Acid (a)

2-[2-[N-(4-Fluoro-3-trifluoromethylphenyl)sulfamoyl]-benzoylamino]-2-hydroxymethylacetic Acid Methyl Ester Under the conditions of Example 2(a), 3.60 g (9.91 mmol) of 4-Fluoro-3-trifluoromethylphenyl)sulfamoyl]-benzoic acid, 1.54 g (9.91 mmol) of L-serine methyl ester hydrochloride, 1.52 g (9.91 mmol) of of hydroxybenzotriazole, hydrate, as well as 1.00 g (9.91 mmol) of triethylamine and 2.04 g (9.91 mmol) of dicyclohexylcarbodiimide are reacted and worked up analogously. The crude product is purified by column chromatography on silica gel. The title compound is eluted with ethyl acetate.

Yield: 3.88 mg (84.3% of theory)
Analysis: $C_{18}H_{16}F_4N_2O_6S$ (464.39):
C,46.56; H,3.47; F,16.36; N,6.03; O,20.67; S,6.90:Calcd.
C,46.46; H,3.69; F,16.31; N,5.90; O,—; S,6.79:Found.

(a)

2-[2-[N-(4-Fluoro-3-trifluoromethylphenyl)sulfamoyl]-benzoylamino]-2-hydroxymethylacetic Acid Under the conditions of Example 4(b), 3.82 g (8.23 mmol) of the ester prepared in 5(a) is saponified in 40 ml of dioxane with 8.5 ml (17 mmol) of 2N barium hydroxide solution, thus obtaining, after an analogous working-up step, the title compound as a material uniform per thin-layer chromatography. The yield is 2.74 g (73.9% of theory).

Analysis: $C_{11}H_{14}F_4N_2O_6S$ (450.36):
C,45.34; H,3.13; F,16.87; N,6.22; O,21.32; S,7.12:Calcd.
C,45.39; H,3.18; F,16.70; N,6.28; O,—; S,7.05:Found.

EXAMPLE 6

2-[2-[N-(4-Fluoro-2-trifluoromethylphenyl)sulfamoyl]acetylamino]-2-methylacetic Acid (a)

2-[2-[N-(4-Fluoro-2-trifluoromethylphenyl)sulfamoyl]acetylamino]-2-methylacetic Acid Ethyl Ester Under the conditions of Example 2(a), 3.012 g (10 mmol) of 2-[2-[N-(4-Fluoro-2-trifluoromethylphenyl)-sulfamoyl]acetic acid, 1.536 g (10 mmol) of L-alanine ethyl ester hydrochloride, 1.531 g (10 mmol) of hydroxybenzotriazole, hydrate, as well as 1.012 g (10 mmol) of triethylamine are reacted and worked up in analogous fashion. The crude product is chromatographed on silica gel. The title compound is eluted with ethyl acetate.

Yield: 2.99 mg (74.6% of theory)
Analysis: $C_{14}H_{10}F_4N_2O_5S$ (400.35):
C,42.00; H,4.03; F,18.98; N,7.00; O,19.98; S,8.01:Calcd.
C,41.83; H,4.11; F,18.90; N,7.07; O,—; S,7.89:Found.

(a)

2-[2-[N-(4-Fluoro-2-trifluoromethylphenyl)sulfamoyl]acetylamino]-2-methylacetic Acid Under the conditions of Example 2(b), 3.203 g (8 mmol) of the ester prepared in 6(a) is saponified with 10 ml (20 mmol) of 2N sodium hydroxide solution in 40 ml of dioxane. The mixture is worked up analogously, thus obtaining 2.418 g (81.2% of theory) of the title compound.

Analysis: $C_{12}H_{12}F_4N_2O_5S$ (372.29):
C,38.72; H,3.25; F,20.41; N,7.52; O,21.49; S,8.61:Calcd.
C,38.81; H,4.11; F,18.90; N,7.07; O,—; S,7.89:Found.

EXAMPLE 7

2-[2-[N-(4-Fluoro-2-trifluoromethylphenyl)sulfamoyl]acetylamino]-2-(1-hydroxyethyl)acetic Acid (a)

2-[2-[N-(4-Fluoro-2-trifluoromethylphenyl)sulfamoyl]acetylamino]-2-(1-hydroxyethyl)acetic Acid Ethyl Ester Under the conditions of Example 2(a), 3.012 g (10 mmol) of 2-[N-(4-fluoro-2-trifluoromethylphenyl)sulfamoyl]acetic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethanol.

Yield: 3.41 g (79.2% of theory)
Analysis: $C_{15}H_{18}F_4N_2O_6S$ (430.37):
C,41.86; H,4.22; F,17.66; N,6.51; O,22.31; S,7.45:Calcd.
C,41.95; H,4.11; F,18.90; N,7.07; O,—; S,7.89:Found.

(a)

2-[2-[N-(4-Fluoro-2-trifluoromethylphenyl)sulfamoyl]acetylamino]-2-(1-hydroxyethyl)acetic Acid Under the conditions of Example 4(b), 1.72 g (4 mmol) of the ester prepared in 7(a) is saponified with 4.5 ml (9 mmol) of 2N barium hydroxide solution in 20 ml of dioxane. The mixture is worked up analogously to 2(b), thus obtaining 1.20 g (74.6% of theory) of the title compound.

Analysis: $C_{13}H_{14}F_4N_2O_6S$ (402.32):
C,38.81; H,3.51; F,18.89; N,6.96; O,23.86; S,7.97:Calcd.
C,38.73; H,3.45; F,18.96; N,7.03; O,—; S,7.90:Found.

EXAMPLE 8

3-[2-[N-(4-Fluoro-2-trifluoromethylphenyl)sulfamoyl]acetylamino]-3-carboxypropionic Acid 3-[2-[N-(4-Fluoro-2-trifluoromethylphenyl)sulfamoyl]acetylamino]-3-carboxypropionic Acid Methyl Ester Under the conditions of Example 2(a), 3.012 g (10 mmol) of 2-[2-[N-(4-fluoro-2-trifluoromethylphenyl)-sulfamoyl]acetic acid, 1.836 g (10 mmol) of L-aspartic acid dimethyl ester hydrochoride, 1,531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.573 g (80.4% of theory)
Analysis: $C_{15}H_{16}F_4N_2O_7S$ (444.36):
C,40.55; H,3.63; F,17.10; N,6.30; O,25.20; S,7.22:Calcd.
C,40.59; H,3.72; F,17.02; N,6.37; O,—; S,7.11:Found.

3-[2-[N-(4-Fluoro-2-trifluoromethylphenyl)sulfamoyl]acetylamino]-3-carboxypropionic Acid Under the conditions of Example 2(b), 2.222 g (5 mmol) of the ester prepared in Example 8(a) is saponified with 8 ml (16 mmol) of 2N sodium hydroxide solution in 20 ml of dioxane. The mixture is worked up analogously to Example 2(b), yielding 1.755 g (84.3% of theory) of the title compound.

Analysis: $C_{13}H_{12}F_4N_2O_7S$ (416.30):
C,37.51; H,2.91; F,18.25; N,6.73; O,26.90; S,7.70:Calcd.
C,37.38; H,2.98; F,18.21; N,6.68; O,—; S,7.61:Found.

EXAMPLE 9

3-[2-[N-(4-Fluoro-2-trifluoromethylphenyl)sulfamoyl]acetylamino]propionic Acid (a)

3-[2-[N-(4-Fluoro-2-trifluoromethylphenyl)sulfamoyl]acetylamino]propionic Acid Ethyl Ester Under the conditions of Example 2(a), 3.012 g (10 mmol) of 2-[2-[N-(4-Fluoro-2-trifluoromethylphenyl)-sulfamoyl]acetic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.259 g (81.4% of theory)
Analysis: $C_{14}H_{16}F_4N_2O_5S$ (400.35);
C,42.00; H,4.03; F,18.98; N,7.00; O,21.49; S,8.61:Calcd.
C,38.81; H,3.27; F,20.32; N,7.61; O,—; S,8.54:Found.

EXAMPLE 10

2-[2-[N-(4-Fluoro-2-trifluoromethylphenyl)sulfamoyl]acetylimino]diacetic Acid (a)

2-[2-[N-(4-Fluoro-2-trifluoromethylphenyl)sulfamoyl]acetylimino]diacetic Acid Diethyl Ester Under the conditions of Example 2(a), 3.012 g (10 mmol) of 2-[N-(4-Fluoro-2-trifluoromethylphenyl)sulfamoyl]acetic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethanol.

Yield: 4.035 g (85.4% of theory)
Analysis: $C_{17}H_{20}F_4N_2O_7S$ (472.41);
C,43.22; H,4.27; F,16.09; N,5.93; O,23.71; S,6.79:Calcd.
C,43.20; H,4.35; F,16.00; N,5.98; O,—; S,6.85:Found.

(b)

2-[2-[N-(4-Fluoro-2-trifluoromethylphenyl)sulfamoyl]acetylimino]diacetic Acid

Under the conditions of Example 2(b), 3.307 g (7 mmol) of the ester produced in 10(a) is saponified with 12 ml (24 mmol) of 2N sodium hydroxide solution in 40 ml of dioxane. The mixture is worked up analogously, thus obtaining 2.436 g (83.6% of theory) of the title compound.

Analysis: $C_{13}H_{12}F_4N_2O_7S$ (416.30);
C,37.15; H,2.91; F,18.25; N,6.73; O,26.90; S,7.70:Calcd.
C,37.38; H,3.00; F,18.18; N,6.80; O,—; S,7.59:Found.
$pK_a$ (37° C.): 6.68 ppm/pH: 4.94 $LD_{50}$ [mmol/kg], mouse:$\leq 7.5$

EXAMPLE 11

2-[4-[N-(4-Fluoro-3-trifluoromethylphenyl)sulfamoyl]benzoylamino]acetic Acid (a)

2-[4-[N-(4-Fluoro-3-trifluoromethylphenyl)sulfamoyl]benzoylamino]acetic Acid Ethyl Ester Under the conditions of Example 2(a), 3.633 g (10 mmol) of 4-[N-(4-fluoro-3-trifluoromethylphenyl)sulfamoyl]benzoic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.69 g (82.3% of theory)
Analysis: $C_{18}H_{16}F_4N_2O_5S$ (448.39);
C,48.22; H,3.60; F,16.95; N,6.25; O,17.84; S,7.15:Calcd.
C,48.15; H,3.71; F,16.87; N,6.20; O,—; S,7.20:Found.

(b)

2-[4-[N-(4-Fluoro-3-trifluoromethylphenyl)sulfamoyl]benzoylamino]acetic Acid

Under the conditions of Example 2(b), 3.139 g (7 mmol) of the ester prepared in Example 11(a) is saponified with 8 ml (16 mmol) of 2N sodium hydroxide solution in 30 ml of dioxane. The mixture is worked up as described in Example 2(b), thus obtaining 2.639 g (80.5% of theory) of the title compound.

Analysis: $C_{16}H_{12}F_4N_2O_5S$ (420.34);
C,45.72; H,2.88; F,18.08; N,6.66; O,19.03; S,7.63:Calcd.
C,45.81; H,2.97; F,18.01; N,6.58; O,—; S,7.55:Found.

EXAMPLE 12

2-[4-[N-(4-Fluoro-3-trifluoromethylphenyl)sulfamoyl]benzoylamino]acetic Acid

2-[4-[N-(4-Fluoro-3-trifluoromethylphenyl)sulfamoyl]benzoylamino]acetic Acid Ethyl Ester Under the conditions of Example 2(a), 3.633 g (10 mmol) of 4[N-(4-fluoro-2-trifluoromethylphenyl)sulfamoyl]benzoic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.553 g (79.2% of theory)
Analysis: $C_{18}H_{16}F_4N_2O_5S$ (448.39);
C,48.22; H,3.60; F,16.95; N,6.25; O,17.84; S,7.15:Calcd.
C,48.13; H,3.67; F,17.00; N,6.31; O,—; S,7.08:Found.

(b)

2-[4-[N-(4-Fluoro-2-trifluoromethylphenyl)sulfamoyl]benzoylamino]acetic Acid

Under the conditions of Example 2(b), 3.139 g (7 mmol) of the ester produced in Example 12(a) is saponified with 8 ml (16 mmol) of 2N sodium hydroxide solution in 30 ml of dioxane. The mixture is worked up analogously, thus obtaining 2.313 g (78.6% of theory) of the title compound.

Analysis: $C_{16}H_{12}F_4N_2O_5S$ (420.34);
C,45.72; H,2.88; F,18.08; N,6.66; O,19.03; S,7.63:Calcd.
C,45.65; H,2.97; F,18.15; N,6.60; O,—; S,7.55:Found.

EXAMPLE 13

(b)

2-[4-[N-(4-Fluoro-2-trifluoromethylphenyl)sulfamoyl]benzoylamino]acetic Acid (b)

2-[4-[N-(4-Fluoro-2-trifluoromethylphenyl)sulfamoyl]benzoylamino]acetic Acid Ethyl Ester Under the conditions of Example 2(a), 3.633 g (10 mmol) of 2-[N-(4-fluoro-2-trifluoromethylphenyl)sulfamoyl]benzoic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.52 g (78.5% of theory)
Analysis: $C_{18}H_{16}F_4N_2O_5S$ (448.39);
C,48.22; H,3.60; F,16.95; N,6.25; O,17.84; S,7.15:Calcd.
C,48.29; H,3.54; F,16.98; N,6.21; O,—; S,7.23:Found.

(b)
2-[2-[N-(4-Fluoro-2-trifluoromethylphenyl)sulfamoyl]-benzoylamino]acetic Acid Under the conditions of Example 2(b), 4.036 g (9 mmol) of the ester produced in Example 13(a) is saponified with 10 ml (20 mmol) of 2N sodium hydroxide solution in 40 ml of dioxane. The mixture is worked up analogously and yields 2.905 g (76.8% of theory) of the title compound.

Analysis: $C_{16}H_{12}F_4N_2O_5S$ (420.34);
C,45.72; H,2.88; F,16.08; N,6.66; O,19.03; S,7.63:Calcd.
C,45.78; H,2.93; F,16.17; N,6.69; O,—; S,7.52:Found.

EXAMPLE 14

2-[2-[N-(4-Fluoro-3-trifluoromethylphenyl)sulfamoyl]-benzoylamino]acetic Acid (a)
2-[2-[N-(4-Fluoro-3-trifluoromethylphenyl)sulfamoyl]-benzoylamino]acetic Acid Ethyl Ester Under the conditions of Example 2(a), 3.633 g (10 mmol) of 2-[N-(4-fluoro-3-trifluoromethylphenyl)sulfamoyl]benzoic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.448 g (76.9% of theory)
Analysis: $C_{18}H_{16}F_4N_2O_5S$ (448.39);
C,48.22; H,3.60; F,16.95; N,6.25; O,17.84; S,7.15:Calcd.
C,48.33; H,3.72; F,17.04; N,6.33; O,—; S,7.04:Found.

(b)
2-[2-[N-(4-Fluoro-3-trifluoromethylphenyl)sulfamoyl]-benzoylamino]acetic Acid Under the conditions of Example 2(b), 2.69 g (6 mmol) of the ester prepared in Example 14(a) is saponified with 6.5 ml (13 mmol) of 2N sodium hydroxide solution in 25 ml of dioxane. The mixture is worked up analogously, thus obtaining 1.977 g (78.4% of theory) of the title compound.

Analysis: $C_{16}H_{12}F_4N_2O_5S$ (420.34);
C,45.72; H,2.88; F,18.08; N,6.66; O,19.03; S,7.63:Calcd.
C,45.80; H,2.95; F,18.01; N,6.59; O,—; S,7.60:Found.

EXAMPLE 15

2-[2-[N-(4-Fluoro-2-trifluoromethylphenyl)sulfamoyl]-benzoylamino]-2-methylacetic Acid (a)
2-[2-[N-(4-Fluoro-2-trifluoromethylphenyl)sulfamoyl]-benzoylamino]-2-methylacetic Acid Ethyl Ester Under the conditions of Example 2(a), 3.633 g (10 mmol) of 4-[N-(4-fluoro-2-trifluoromethylphenyl)sulfamoyl]benzoic acid, 1.536 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.672 g (79.4% of theory)
Analysis: $C_{19}H_{18}F_4N_2O_5S$ (462.42);
C,49.35; H,3.92; F,16.43; N,6.06; O,17.30; S,6.93:Calcd.
C,49.29; H,3.98; F,16.45; N,6.11; O,—; S,6.88:Found.

(b)
2-[4-[N-(4-Fluoro-2-trifluoromethylphenyl)sulfamoyl]-benzoylamino]-2-methylacetic Acid Under the conditions of Example 2(b), 3.237 g (7 mmol) of the ester prepared in Example 15(a) is saponified with 7.5 ml (15 mmol) of 2N sodium hydroxide solution in 30 ml of dioxane. The mixture is worked up analogously, thus obtaining 2.399 g (78.9% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,46.93; H,3.32; F,17.44; N,6.51; O,—; S,7.30:Found.

EXAMPLE 16

2-[4-[N-(4-Fluoro-2-trifluoromethylphenyl)sulfamoyl]-benzoylamino]-2-methylacetic Acid (a)
2-[4-[N-(4-Fluoro-2-trifluoromethylphenyl)sulfamoyl]-benzoylamino]-2-methylacetic Acid Ethyl Ester Under the conditions of Example 2(a), 3.633 g (10 mmol) of 2-[N-(4-fluoro-3l-trifluoromethylphenyl)sulfamoyl]benzoic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.593 g (77.7% of theory)
Analysis: $C_{19}H_{16}F_4N_2O_5S$ (462.42);
C,49.35; H,3.92; F,16.43; N,6.06; O,17.30; S,6.93:Calcd.
C,49.30; H,3.96; F,16.40; N,6.10; O,—; S,6.88:Found.

(b)
2-[4-[N-(4-Fluoro-2-trifluoromethylphenyl)sulfamoyl]-benzoylamino]-2-methylacetic Acid Under the conditions of Example 2(b), 2.312 g (5 mmol) of the ester produced in Example 16(a) is saponified with 3 ml (6 mmol) of 2N sodium hydroxide solution in 20 ml of dioxane. The mixture is worked up in analogous fashion, yielding 1.677 g (77.2% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,47.11; H,3.30; F,17.60; N,6.36; O,—; S,7.29:Found.

EXAMPLE 17

2-[2-[N-(4-Fluoro-3-trifluoromethylphenyl)sulfamoyl]-benzoylamino]-2-methylacetic Acid (a)
2-[2-[N-(4-Fluoro-3-trifluoromethylphenyl)sulfamoyl]-benzoylamino]-2-methylacetic Acid Ethyl Ester Under the conditions of Example 2(a), 3.633 g (10 mmol) of 2-[N-(4-fluoro-3-trifluoromethylphenyl)sulfamoyl]benzoic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously.

The crude product is chromatographed on silica gel. The title compound is eluted with ethyl acetate.

Yield: 3.625 g (78.4% of theory)

Analysis: $C_{19}H_{18}F_4N_2O_5S$ (462.42);
C,49.35; H,3.92; F,16.43; N,6.06; O,17.30; S,6.93:Calcd.
C,49.42; H,3.99; F,16.38; N,6.11; O,—; S,6.86:Found.

(b)

2-[2-[N-(4-Fluoro-3-trifluoromethylphenyl)sulfamoyl]-benzoylamino]-2-methylacetic Acid Under the conditions of Example 2(b), 2.775 g (6 mmol) of the ester prepared in Example 17(a) is saponified with 6.5 ml (13 mmol) of 2N sodium hydroxide solution in 25 ml of dioxane. The mixture is worked up analogously, thus obtaining 2.004 g (76.9% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,47.08; H,3.32; F,17.40; N,6.51; O,—; S,7.28:Found.

EXAMPLE 18

2-[2-[N-(4-Fluoro-2-trifluoromethylphenyl)sulfamoyl]-benzoylamino]-2-methylacetic Acid (a)

2-[2-[N-(4-Fluoro-2-trifluoromethylphenyl)sulfamoyl]-benzoylamino]-2-methylacetic Acid Ethyl Ester Under the conditions of Example 2(a), 3.633 g (10 mmol) of 2-[N-(4-fluoro-2-trifluoromethylphenyl)sulfamoyl]benzoic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.796 g (82.1% of theory)

Analysis: $C_{19}H_{18}F_4N_2O_5S$ (462.42);
C,49.35; H,3.92; F,16.43; N,6.06; O,17.30; S,6.93:Calcd.
C,49.47; H,3.97; F,16.48; N,6.03; O,—; S,6.90:Found.

(b)

2-[2-[N-(4-Fluoro-2-trifluoromethylphenyl)sulfamoyl]-benzoylamino]-2-methylacetic Acid Under the conditions of Example 2(b), 3.70 g (8 mmol) of the ester prepared in Example 18(a) is saponified with 8.5 ml (17 mmol) of 2N sodium hydroxide solution in 35 ml of dioxane. The mixture is worked up analogously, thus obtaining 2.804 g (80.7% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,46.92; H,3.32; F,17.54; N,6.51; O,—; S,7.29:Found.

EXAMPLE 19

2-[4-[N-(4-Fluoro-2-trifluoromethylphenyl)sulfamoyl]-benzoylamino]-2-hydroxymethylacetic Acid (a)

2-[4-[N-(4-Fluoro-2-trifluoromethylphenyl)sulfamoyl]-benzoylamino]-2-hydroxymethylacetic Acid Methyl Ester Under the conditions of Example 2(a), 3.633 g (10 mmol) of 4-[N-(4-fluoro-2-trifluoromethylphenyl)sulfamoyl]benzoic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.478 g (74.9% of theory)

Analysis: $C_{18}H_{16}F_4N_2O_6S$ (464.39);
C,46.56; H,3.47; F,16.36; N,6.03; O,20.67; S,6.90:Calcd.
C,46.62; H,3.54; F,16.30; N,6.09; O,—; S,6.87:Found.

(b)

2-[4-[N-(4-Fluoro-2-trifluoromethylphenyl)sulfamoyl]-benzoylamino]-2-hydroxymethylacetic Acid Under the conditions of Example 4(b), 3.70 g (8 mmol) of the ester prepared in Example 19(a) is saponified with 6.5 ml (13 mmol) of 2N sodium hydroxide solution in 25 ml of dioxane. The mixture is worked up analogously, thus obtaining 2.119 g (78.4% of theory) of the title compound.

Analysis: $C_{17}H_{14}F_4N_2O_6S$ (450.37);
C,45.34; H,3.13; F,16.87; N,6.22; O,21.32; S,7.12:Calcd.
C,45.26; H,3.18; F,16.81; N,6.29; O,—; S,7.07:Found.

EXAMPLE 20

2-[2-[N-(4-Fluoro-3-trifluoromethylphenyl)sulfamoyl]-benzoylamino]-2-hydroxymethylacetic Acid (a)

2-[2-[N-(4-Fluoro-3-trifluoromethylphenyl)sulfamoyl]-benzoylamino]-2-hydroxymethylacetic Acid Methyl Ester Under the conditions of Example 2(a), 3.633 g (10 mmol) of 4-[N-(4-fluoro-2-trifluoromethylphenyl)sulfamoyl]benzoic acid, 1.556 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.646 g (78.5% of theory)

Analysis: $C_{18}H_{16}F_4N_2O_6S$ (464.39);
C,46.56; H,3.47; F,16.36; N,6.03; O,20.67; S,6.90:Calcd.
C,46.60; H,3.52; F,16.38; N,6.11; O,—; S,6.92:Found.

(b)

2-[2-[N-(4-Fluoro-3-trifluoromethylphenyl)sulfamoyl]-benzoylamino]-2-hydroxymethylacetic Acid Under the conditions of Example 4(b), 2.090 g (4.5 mmol) of the ester prepared in Example 20(a) is saponified with 5 ml (10 mmol) of 2N sodium hydroxide solution in 20 ml of dioxane. The mixture is worked up analogously, thus obtaining 1.552 g (76.6% of theory) of the title compound.

Analysis: $C_{17}H_{14}F_4N_2O_6S$ (450.37);
C,45.34; H,3.13; F,16.87; N,6.22; O,21.32; S,7.12:Calcd.
C,45.27; H,3.19; F,16.80; N,6.29; O,—; S,7.03:Found.

EXAMPLE 21

2-[2-[N-(4-Fluoro-2-trifluoromethylphenyl)sulfamoyl]-benzoylamino]-2-hydroxymethylacetic Acid (a)

2-[2-[N-(4-Fluoro-2-trifluoromethylphenyl)sulfamoyl]-benzoylamino]-2-hydroxymethylacetic Acid Methyl Ester Under the conditions of Example 2(a), 3.633 g (10 mmol) of 2-[N-(4-fluoro-2-trifluoromethylphenyl)sulfamoyl]benzoic acid, 1.556 g (10 mmol) of L-serine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.673 g (79.1% of theory)

Analysis: $C_{18}H_{16}F_4N_2O_6S$ (464.39);

C,46.56;  H,3.47;  F,16.36;  N,6.03;  O,20.67; S,6.90:Calcd.

C,46.50; H,3.55; F,16.30; N,6.10; O,—; S,6.85:Found.

(b)

2-[2-[N-(4-Fluoro-2-trifluoromethylphenyl)sulfamoyl]-benzoylamino]-2-hydroxymethylacetic Acid Under the conditions of Example 4(b), 3.251 g (7 mmol) of the ester prepared in Example 21(a) is saponified with 8 ml (16 mmol) of 2N sodium hydroxide solution in 35 ml of dioxane. The mixture is worked up analogously, yielding (2.465 g (78.2% of theory) of the title compound.

Analysis: $C_{17}H_{14}F_4N_2O_6S$ (450.37);

C,45.34;  H,3.13;  F,16.87;  N,6.22;  O,21.32; S,7.12:Calcd.

C,45.30; H,3.18; F,16.81; N,6.27; O,—; S,7.09:Found.

EXAMPLE 22

2-[2-[N-(4-Fluoro-3-trifluoromethylphenyl)sulfamoyl]-benzoylamino]-2-methylacetic Acid (a)

2-[2-[N-(4-Fluoro-3-trifluoromethylphenyl)sulfamoyl]-benzoylamino]-2-methylacetic Acid Ethyl Ester Under the conditions of Example 2(a), 3.012 g (10 mmol) of 2-[N-(4-fluoro-3-trifluoromethylphenyl)sulfamoyl]acetic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.055 g (76.3% of theory)

Analysis: $C_{14}H_{16}F_4N_2O_5S$ (400.35);

C,42.00;  H,4.03;  F,18.98;  N,7.00;  O,19.98; S,8.01:Calcd.

C,41.88; H,4.09; F,19.91; N,7.02; O,—; S,8.05:Found.

(b)

2-[2-[N-(4-Fluoro-3-trifluoromethylphenyl)sulfamoyl]-benzoylamino]-2-methylacetic Acid Under the conditions of Example 2(b), 3.003 g (7.5 mmol) of the ester prepared in Example 22(a) is saponified with 8 ml (16 mmol) of 2N sodium hydroxide solution in 35 ml of dioxane. The mixture is worked up analogously, thus obtaining 2.195 g (78.6% of theory) of the title compound.

Analysis: $C_{12}H_{12}F_4N_2O_5S$ (372.29);

C,38.72;  H,3.25;  F,20.41;  N,7.52;  O,21.49; S,8.61:Calcd.

C,38.68; H,3.29; F,20.35; N,7.44; O,—; S,8.53:Found.

EXAMPLE 23

2-[2-[N-(4-Fluoro-3-trifluoromethylphenyl)sulfamoyl]acetylamino]-2-(1-hydroxyethyl)acetic Acid (a)

2-[2-[N-(4-Fluoro-3-trifluoromethylphenyl)sulfamoyl]acetylamino]-2-(1-hydroxyethyl)acetic Acid Ethyl Ester Under the conditions of Example 2(a), 3.012 g (10 mmol) of 2-[N-(4-fluoro-3-trifluoromethylphenyl)sulfamoyl]acetic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.391 g (78.8% of theory)

Analysis: $C_{15}H_{18}F_4N_2O_6S$ (430.37);

C,41.86;  H,4.22;  F,17.66;  N,6.51;  O,22.31; S,7.45:Calcd.

C,41.80; H,4.28; F,17.62; N,6.57; O,—; S,7.49:Found.

(b)

2-[2-[N-(4-Fluoro-3-trifluoromethylphenyl)sulfamoyl]acetylamino]-2-(1-hydroxyethyl)acetic Acid Under the conditions of Example 4(b), 3.142 g (7.3 mmol) of the ester prepared in Example 23(a) is saponified with 8 ml (16 mmol) of 2N sodium hydroxide solution in 30 ml of dioxane. The mixture is worked up analogously to Example 2(b), thus producing 2.285 g (77.8% of theory) of the title compound.

Analysis: $C_{13}H_{14}F_4N_2O_6S$ (402.32);

C,38.81;  H,3.51;  F,18.89;  N,6.96;  O,23.86; S,7.97:Calcd.

C,38.84; H,3.59; F,18.81; N,6.89; O,—; S,7.99:Found.

EXAMPLE 24

3-[2-[N-(4-Fluoro-3-trifluoromethylphenyl)sulfamoyl]acetylamino]-3-carboxypropionic Acid (a)

3-[2-[N-(4-Fluoro-3-trifluoromethylphenyl)sulfamoyl]acetylamino]-3-methoxycarbonylpropionic Acid Methyl Ester Under the conditions of Example 2(a), 3.012 g (10 mmol) of 2-[N-(4-fluoro-3-trifluoromethylphenyl)sulfamoyl]acetic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.475 g (78.2% of theory)

Analysis: $C_{15}H_{16}F_4N_2O_7S$ (444.36);

C,40.55;  H,3.63;  F,17.10;  N,6.30;  O,25.20; S,7.22:Calcd.

C,40.48; H,3.65; F,17.00; N,6.24; O,—; S,7.15:Found.

(b)
3-[2-[N-(4-Fluoro-3-trifluoromethylphenyl)sulfamoyl-]acetylamino]-3-carboxypropionic Acid Under the conditions of Example 2(b), 2.888 g (6.5 mmol) of the ester produced in Example 24(a) is saponified with 11 ml (22 mmol) of 2N sodium hydroxide solution in 40 ml of dioxane. The mixture is worked up analogously to Example 2(b), yielding 2.219 g (82.0% of theory) of the title compound.

Analysis: $C_{13}H_{12}F_4N_2O_7S$ (416.30);
C,37.51;   H,2.91;   F,18.25;   N,6.73;   O,26.90; S,7.70:Calcd.
C,37.58; H,2.99; F,18.20; N,6.70; O,—; S,7.64:Found.

EXAMPLE 25

3-[2-[N-(4-Fluoro-3-trifluoromethylphenyl)sulfamoyl-]acetylamino]propionic Acid (a)
3-[2-[N-(4-Fluoro-3-trifluoromethylphenyl)sulfamoyl-]acetylamino]propionic Acid Ethyl Ester Under the conditions of Example 2(a), 3.012 g (10 mmol) of 2-[N-(4-fluoro-3-trifluoromethylphenyl)sulfamoyl]acetic acid, 1.536 g (10 mmol) of β-alanine ethyl acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.27 g (81.9% of theory)
Analysis: $C_{14}H_{16}F_4N_2O_5S$ (400.35);
C,42.00;   H,4.03;   F,18.98;   N,7.00;   O,19.98; S,8.01:Calcd.
C,41.95; H,4.10; F,18.89; N,7.10; O,—; S,8.06:Found.

(b)
3-[2-[N-(4-Fluoro-3-trifluoromethylphenyl)sulfamoyl-]acetylamino]propionic Acid Under the conditions of Example 2(b), 2.522 g (6.3 mmol) of the ester produced in Example 25(a) is saponified with 7 ml (14 mmol) of 2N sodium hydroxide solution in 25 ml of dioxane. The mixture is worked up analogously to Example 2(b), thus obtaining 1.872 g (79.8% of theory) of the title compound.

Analysis: $C_{12}H_{12}F_4N_2O_5S$ (372.29);
C,38.72;   H,3.25;   F,20.41;   N,7.52;   O,21.49; S,8.61:Calcd.
C,38.77; H,3.30; F,20.44; N,7.48; O,—; S,8.60:Found.

EXAMPLE 26

2-[2-[N-(4-Fluoro-3-trifluoromethylphenyl)sulfamoyl-]acetylimino]diacetic Acid (a)
2-[2-[N-(4-Fluoro-3-trifluoromethylphenyl)sulfamoyl]-benzoylimino]diacetic Acid Diethyl Ester Under the conditions of Example 2(a), 3.012 g (10 mmol) of 2-[N-(4-fluoro-3-trifluoromethylphenyl)sulfamoyl]acetic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.812 g (80.7% of theory)

Analysis: $C_{17}H_{20}F_4N_2O_7S$ (472.41);
C,43.22;   H,4.27;   F,16.09;   N,5.93;   O,23.71; S,6.79:Calcd.
C,43.27; H,4.34; F,16.03; N,5.88; O,—; S,6.72:Found.

(b)
2-[2-[N-(4-Fluoro-3-trifluoromethylphenyl)sulfamoyl-]acetylamino]diacetic Acid Under the conditions of Example 2(b), 3.307 g (7 mmol) of the ester produced in Example 26(a) is saponified with 12 ml (24 mmol) of 2N sodium hydroxide solution in 35 ml of dioxane. The mixture is worked up analogously to Example 2(b), yielding 2.404 g (82.5% of theory) of the title compound.

Analysis: $C_{13}H_{12}F_4N_2O_7S$ (416.30);
C,37.51;   H,2.91;   F,18.25;   N,6.73;   O,26.90; S,7.70:Calcd.
C,37.60; H,2.99; F,18.20; N,6.62; O,—; S,7.62:Found.

EXAMPLE 27

2-[2-[N-(4-Fluoro-3-trifluoromethylphenyl)sulfamoyl]-benzoylamino]-2-(1-hydroxyethyl)acetic Acid (a)
2-[2-[N-(4-Fluoro-3-trifluoromethylphenyl)sulfamoyl]-benzoylamino]-2-(1-hydroxyethyl)acetic Acid Ethyl Ester Under the conditions of Example 2(a), 3.633 g (10 mmol) of 4-[N-(4-Fluoro-3-trifluoromethylphenyl)sulfamoyl]benzoic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.954 g (80.3% of theory)
Analysis: $C_{20}H_{20}F_4N_2O_6S$ (492.45);
C,48.78;   H,4.09;   F,15.43;   N,5.69;   O,19.49; S,6.51:Calcd.
C,48.86; H,4.15; F,15.38; N,5.77; O,—; S,6.55:Found.

(b)
2-[4-[N-(4-Fluoro-3-trifluoromethylphenyl)sulfamoyl]-benzoylamino]-2-(1-hydroxyethyl)acetic Acid Under the conditions of Example 4(b), 2.61 g (5.3 mmol) of the ester produced in Example 27(a) is saponified with 6 ml (12 mmol) of 2N barium hydroxide solution in 25 ml of dioxane. The mixture is worked up analogously thus producing 1.935 g (78.6% of theory) of the title compound.

Analysis: $C_{18}H_{16}F_4N_2O_6S$ (464.39);
C,46.54;   H,3.47;   F,16.36;   N,6.03;   O,20.67; S,6.90:Calcd.
C,46.66; H,3.54; F,16.45; N,6.08; O,—; S,6.79:Found.

EXAMPLE 28

2-[4-[N-(4-Fluoro-3-trifluoromethylphenyl)sulfamoyl]-benzoylamino]-2-(1-hydroxyethyl)acetic Acid (a)
2-[4-[N-(4-Fluoro-3-trifluoromethylphenyl)sulfamoyl]-benzoylamino]-2-(1-hydroxyethyl)acetic Acid Ethyl Ester Under the conditions of Example 2(a), 3.633 g (10 mmol) of 4-[N-(4-fluoro-2-trifluoromethylphenyl)sulfamoyl]]benzoic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.856 g (78.3% of theory)
Analysis: $C_{20}H_{20}F_4N_2O_6S$ (492.45);
C,48.78; H,4.09; F,15.43; N,5.69; O,19.49; S,6.51:Calcd.
C,48.71; H,4.15; F,15.36; N,5.62; O,—; S,6.43:Found.

(b)

2-[4-[N-(4-Fluoro-3-trifluoromethylphenyl)sulfamoyl]-benzoylamino]-2-(1-hydroxyethyl)acetic Acid Under the conditions of Example 4(b), 3.94 g (8 mmol) of the ester produced in Example 28(a) is saponified with 8.5 ml (17 mmol) of 2N barium hydroxide solution in 40 ml of dioxane. The mixture is worked up analogously thus obtaining 2.905 g (78.2% of theory) of the title compound.

Analysis: $C_{18}H_{16}F_4N_2O_6S$ (464.39);
C,46.56; H,3.47; F,16.36; N,6.03; O,20.67; S,6.90:Calcd.
C,46.48; H,3.53; F,16.31; N,6.07; O,—; S,6.85:Found.

EXAMPLE 29

2-[2-[N-(4-Fluoro-3-trifluoromethylphenyl)sulfamoyl]-benzoylamino]-2-(1-hydroxyethyl)acetic Acid (a)

2-[2-[N-(4-Fluoro-3-trifluoromethylphenyl)sulfamoyl]-benzoylamino]-2-(1-hydroxyethyl)acetic Acid Ethyl Ester Under the conditions of Example 2(a), 3.633 g (10 mmol) of 2-[N-(4-fluoro-3-trifluoromethylphenyl)sulfamoyl]benzoic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.969 g (80.6% of theory)
Analysis: $C_{20}H_{20}F_4N_2O_6S$ (492.45);
C,48.78; H,4.09; F,15.43; N,5.69; O,19.49; S,6.51:Calcd.
C,48.85; H,4.17; F,15.38; N,5.66; O,—; S,6.45:Found.

(b)

2-[2-[N-(4-Fluoro-2-trifluoromethylphenyl)sulfamoyl]-benzoylamino]-2-(1-hydroxyethyl)acetic Acid Under the conditions of Example 4(b), 3.447 g (7 mmol) of the ester produced in Example 29(a) is saponified with 7.5 ml (15 mmol) of 2N barium hydroxide solution in 30 ml of dioxane. The mixture is worked up analogously, yielding 2.581 g (79.4% of theory) of the title compound.

Analysis: $C_{18}H_{16}F_4N_2O_6S$ (464.39);
C,46.56; H,3.47; F,16.36; N,6.03; O,20.67; S,6.90:Calcd.
C,46.60; H,3.52; F,16.30; N,6.00; O,—; S,6.83:Found.

EXAMPLE 30

2-[2-[N-(4-Fluoro-2-trifluoromethylphenyl)sulfamoyl]-benzoylamino]-2-(1-hydroxyethyl)acetic Acid (a)

2-[2-[N-(4-Fluoro-2-trifluoromethylphenyl)sulfamoyl]-benzoylamino]-2-(1-hydroxyethyl)acetic Acid Ethyl Ester Under the conditions of Example 2(a), 3.633 g (10 mmol) of 2-[N-(4-Fluoro-2-trifluoromethylphenyl)sulfamoyl]benzoic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.881 g (78.8% of theory)
Analysis: $C_{20}H_{20}F_4N_2O_6S$ (492.45);
C,48.78; H,4.09; F,15.43; N,5.69; O,19.49; S,6.51:Calcd.
C,48.76; H,4.14; F,15.40; N,5.73; O,—; S,6.47:Found.

(b)

2-[2-[N-(4-Fluoro-2-trifluoromethylphenyl)sulfamoyl]-benzoylamino]-2-(1-hydroxyethyl)acetic Acid Under the conditions of Example 4(b), 2.955 g (6 mmol) of the ester produced in Example 30(a) is saponified with 6.5 ml (13 mmol) of 2N barium hydroxide solution in 30 ml of dioxane. The mixture is worked up analogously thus obtaining 2.143 g (76.9% of theory) of the title compound.

Analysis: $C_{18}H_{16}F_4N_2O_6S$ (464.39);
C,46.56; H,3.47; F,16.36; N,6.03; O,20.67; S,6.90:Calcd.
C,46.50; H,3.49; F,16.31; N,6.08; O,—; S,6.84:Found.

EXAMPLE 31

3-[4-[N-(4-Fluoro-3-trifluoromethylphenyl)sulfamoyl]-benzoylamino]-3-carboxypropionic Acid (a)

3-[4-[N-(4-Fluoro-3-trifluoromethylphenyl)sulfamoyl]-benzoylamino]-3-methoxycarbonylpropionic Acid Methyl Ester Under the conditions of Example 2(a), 3.633 g (10 mmol) of 4-[N-(4-fluoro-3-trifluoromethylphenyl)sulfamoyl]benzoic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.138 g (81.7% of theory)
Analysis: $C_{20}H_{18}F_4N_2O_7S$ (506.43);
C,47.43; H,3.58; F,15.01; N,5.53; O,22.11; S,6.33:Calcd.
C,47.37; H,3.63; F,15.04; N,5.48; O,—; S,6.29:Found.

(b)

3-[4-[N-(4-Fluoro-3-trifluoromethylphenyl)sulfamoyl]-benzoylamino]-3-carboxypropionic Acid Under the conditions of Example 2(b), 3.039 g (6 mmol) of the ester produced in Example 31(a) is saponified with 7 ml (14 mmol) of 2N sodium hydroxide solution in 40 ml of dioxane. The product is worked up analogously, yielding 2.365 g (82.4% of theory) of the title compound.

Analysis: $C_{18}H_{14}F_4N_2O_7S$ (478.38);
C,45.19; H,2.95; F,15.88; N,5.86; O,23.41; S,6.70:Calcd.
C,45.22; H,3.00; F,15.83; N,5.79; O,—; S,6.63:Found.

EXAMPLE 32

3-[4-[N-(4-Fluoro-3-trifluoromethylphenyl)sulfamoyl]-benzoylamino]-3-carboxypropionic Acid (a)

3-[4-[N-(4-Fluoro-3-trifluoromethylphenyl)sulfamoyl]-benzoylamino]-3-methoxycarbonylpropionic Acid Methyl Ester Under the conditions of Example 2(a), 3.633 g (10 mmol) of 4-[N-(4-fluoro-3-trifluoromethylphenyl)sulfamoyl]benzoic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.046 g (79.9% of theory)
Analysis: $C_{20}H_{18}F_4N_2O_7S$ (506.43);
C,47.43; H,3.58; F,15.01; N,5.53; O,22.11; S,6.33:Calcd.
C,47.46; H,3.69; F,14.96; N,5.48; O,—; S,6.27:Found.

(b)

3-[4-[N-(4-Fluoro-2-trifluoromethylphenyl)sulfamoyl]-benzoylamino]-3-carboxypropionic Acid Under the conditions of Example 2(b), 3.039 g (6 mmol) of the ester produced in Example 32(a) is saponified with 7 ml (14 mmol) of 2N sodium hydroxide solution in 30 ml of dioxane. The product is worked up analogously, yielding 2.354 g (82.0% of theory) of the title compound.

Analysis: $C_{18}H_{14}F_4N_2O_7S$ (478.38);
C,45.19; H,2.95; F,15.88; N,5.86; O,23.41; S,6.70:Calcd.
C,45.14; H,2.99; F,15.79; N,5.90; O,—; S,6.59:Found.

EXAMPLE 33

3-[2-[N-(4-Fluoro-3-trifluoromethylphenyl)sulfamoyl]-benzoylamino]propionic Acid (a)

3-[2-[N-(4-Fluoro-3-trifluoromethylphenyl)sulfamoyl]-benzoylamino]propionic Acid Ethyl Ester Under the conditions of Example 2(a), 3.633 g (10 mmol) of 2-[N-(4-fluoro-3-trifluoromethylphenyl)sulfamoyl]benzoic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.806 g (82.3% of theory)
Analysis: $C_{19}H_{18}F_4N_2O_5S$ (462.42);
C,49.35; H,3.92; F,16.43; N,6.06; O,17.30; S,6.93:Calcd.
C,49.40; H,3.98; F,16.40; N,6.03; O,—; S,6.88:Found.

(b)

3-[2-[N-(4-Fluoro-3-trifluoromethylphenyl)sulfamoyl]-benzoylamino]propionic Acid Under the conditions of Example 2(b), 3.329 g (7.2 mmol) of the ester prepared in Example 33(a) is saponified with 8 ml (16 mmol) of 2N sodium hydroxide solution in 40 ml of dioxane. The mixture is worked up analogously, thus obtaining 2.527 g (80.8% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,46.95; H,3.31; F,17.43; N,6.50; O,—; S,7.33:Found.

EXAMPLE 34

3-[2-[N-(4-Fluoro-2-trifluoromethylphenyl)sulfamoyl]-benzoylamino]propionic Acid (a)

3-[2-[N-(4-Fluoro-2-trifluoromethylphenyl)sulfamoyl]-benzoylamino]propionic Acid Ethyl Ester Under the conditions of Example 2(a), 3.633 g (10 mmol) of 2-[N-(4-fluoro-2-trifluoromethylphenyl)sulfamoyl]benzoic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 3.733 g (81.6% of theory)
Analysis: $C_{19}H_{18}F_4N_2O_5S$ (462.42);
C,49.35; H,3.92; F,16.43; N,6.06; O,17.30; S,6.93:Calcd.
C,49.31; H,3.97; F,16.39; N,6.10; O,—; S,6.97:Found.

(b)

3-[2-[N-(4-Fluoro-2-trifluoromethylphenyl)sulfamoyl]-benzoylamino]propionic Acid Under the conditions of Example 2(b), 2.960 g (6.4 mmol) of the ester produced in Example 34(a) is saponified with 7 ml (14 mmol) of 2N sodium hydroxide solution in 30 ml of dioxane. The mixture is worked up analogously, yielding 2.213 g (79.6% of theory) of the title compound.

Analysis: $C_{17}H_{14}F_4N_2O_5S$ (434.37);
C,47.01; H,3.25; F,17.49; N,6.45; O,18.42; S,7.38:Calcd.
C,47.10; H,3.31; F,17.42; N,6.52; O,—; S,7.28:Found.

EXAMPLE 35

3-[2-[N-(4-Fluoro-3-trifluoromethylphenyl)sulfamoyl]-benzoylamino]-3-carboxypropionic Acid (a)

3-[2-[N-(4-Fluoro-3-trifluoromethylphenyl)sulfamoyl]-benzoylamino]-3-methoxycarbonylpropionic Acid Methyl Ester Under the conditions of Example 2(a), 3.633 g (10 mmol) of 2-[N-(4-fluoro-3-trifluoromethylphenyl)sulfamoyl]benzoic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.107 g (81.1% of theory)
Analysis: $C_{20}H_{18}F_4N_2O_7S$ (506.42);
C,47.43;   H,3.58;   F,15.01;   N,5.53;   O,22.11; S,6.33:Calcd.
C,47.51; H,3.66; F,15.00; N,5.48; O,—; S,6.27:Found.

(b)
3-[2-[N-(4-Fluoro-3-trifluoromethylphenyl)sulfamoyl]-benzoylamino]-3-carboxypropionic Acid Under the conditions of Example 2(b), 2.887 g (5.7 mmol) of the ester produced in Example 35(a) is saponified with 7 ml (14 mmol) of 2N sodium hydroxide solution in 35 ml of dioxane. The mixture is worked up analogously, thus obtaining 2.203 g (80.8% of theory) of the title compound.
Analysis: $C_{18}H_{14}F_4N_2O_7S$ (478.38);
C,45.19;   H,2.95;   F,15.88;   N,5.86;   O,23.41; S,6.70:Calcd.
C,45.14; H,2.89; F,15.82; N,5.90; O,—; S,6.58:Found.

EXAMPLE 36

3-[2-[N-(4-Fluoro-2-trifluoromethylphenyl)sulfamoyl]-benzoylamino]-3-carboxypropionic Acid (a)
3-[2-[N-(4-Fluoro-2-trifluoromethylphenyl)sulfamoyl]-benzoylamino]-3-methoxycarbonylpropionic Acid Methyl Ester Under the conditions of Example 2(a), 3.633 g (10 mmol) of 2-[N-(4-fluoro-2-trifluoromethylphenyl)sulfamoyl]benzoic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.
Yield: 4.046 g (79.9% of theory)
Analysis: $C_{20}H_{18}F_4N_2O_7S$ (506.43);
C,47.43;   H,3.58;   F,15.01;   N,5.53;   O,22.11; S,6.33:Calcd.
C,47.38; H,3.64; F,14.94; N,5.50; O,—; S,6.26:Found.

(b)
3-[2-[N-(4-Fluoro-2-trifluoromethylphenyl)sulfamoyl]-benzoylamino]-3-carboxypropionic Acid Under the conditions of Example 2(b), 3.039 g (6 mmol) of the ester prepared in Example 36(a) is saponified with 6.5 ml (13 mmol) of 2N sodium hydroxide solution in 30 ml of dioxane. The mixture is worked up analogously, thus obtaining 2.265 g (78.9% of theory) of the title compound.
Analysis: $C_{18}H_{14}F_4N_2O_7S$ (478.38);
C,45.19;   H,2.95;   F,15.88;   N,5.86;   O,23.41; S,6.70:Calcd.
C,45.31; H,3.08; F,15.74; N,5.91; O,—; S,6.58:Found.

EXAMPLE 37

3-[4-[N-(4-Fluoro-3-trifluoromethylphenyl)sulfamoyl]-benzoylamino]propionic Acid (a)
3-[4-[N-(4-Fluoro-3-trifluoromethylphenyl)sulfamoyl]-benzoylamino]propionic Acid Ethyl Ester Under the conditions of Example 2(a), 3.633 g (10 mmol) of 2-[N-(4-fluoro-3-trifluoromethylphenyl)sulfamoyl]benzoic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up in analogous fashion. The crude product is chromatographed on silica gel. The title compound is eluted with ethyl acetate.
Yield: 3.635 g (78.6% of theory)
Analysis: $C_{19}H_{18}F_4N_2O_5S$ (462.42);
C,49.35;   H,3.92;   F,16.43;   N,6.06;   O,17.30; S,6.93:Calcd.
C,49.48; H,3.98; F,16.37; N,6.12; O,—; S,6.85:Found.

(b)
3-[4-[N-(4-Fluoro-3-trifluoromethylphenyl)sulfamoyl]-benzoylamino]propionic Acid Under the conditions of Example 2(b), 2.405 g (5.2 mmol) of the ester produced in Example 37(a) is saponified with 6 ml (12 mmol) of 2N sodium hydroxide solution in 25 ml of dioxane. The mixture is worked up analogously, yielding 1.843 g (81.6% of theory) of the title compound.
Analysis: $C_{17}H_{14}F_4N_2O_5S$ (434.37);
C,47.01;   H,3.25;   F,17.49;   N,6.45;   O,18.42; S,7.38:Calcd.
C,47.08; H,3.31; F,17.49; N,6.40; O,—; S,7.31:Found.

EXAMPLE 38

3-[4-[N-(4-Fluoro-2-trifluoromethylphenyl)sulfamoyl]-benzoylamino]propionic Acid (a)
3-[4-[N-(4-Fluoro-2-trifluoromethylphenyl)sulfamoyl]-benzoylamino]propionic Acid Ethyl Ester Under the conditions of Example 2(a), 3.633 g (10 mmol) of 4-[N-(4-fluoro-2-trifluoromethylphenyl)sulfamoyl]benzoic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel and the title compound eluted with ethyl acetate.
Yield: 3.57 g (77.2% of theory)
Analysis: $C_{19}H_{18}F_4N_2O_5S$ (462.42);
C,49.35;   H,3.92;   F,16.43;   N,6.06;   O,17.30; S,6.93:Calcd.
C,49.27; H,3.96; F,16.36; N,6.11; O,—; S,6.84:Found.

(b)
3-[4-[N-(4-Fluoro-2-trifluoromethylphenyl)sulfamoyl]-benzoylamino]propionic Acid Under the conditions of Example 2(b), 2.821 g (6.1 mmol) of the ester prepared in Example 38(a) is saponified with 7 ml (14 mmol) of 2N sodium hydroxide solution in 30 ml of dioxane. The mixture is worked up analogously, yielding 2.08 g (78.5% of theory) of the title compound.
Analysis: $C_{17}H_{14}F_4N_2O_5S$ (434.37)
C,47.01;   H,3.25;   F,17.49;   N,6.45;   O,18.42; S,7.38:Calcd.
C,46.90; H,3.33; F,17.40; N,6.51; O,—; S,7.31:Found.

EXAMPLE 39

2-[2-[N-(4-Fluoro-2-trifluoromethylphenyl)sulfamoyl]-benzoylimino]diacetic Acid

(a)

2-[2-[N-(4-Fluoro-2-trifluoromethylphenyl)sulfamoyl]-benzoylimino]diacetic Acid Diethyl Ester

Under the conditions of Example 2(a), 3.633 g (10 mmol) of 2-[N-(4-fluoro-2-trifluoromethylphenyl)sulfamoyl]benzoic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.420 g (82.7% of theory)
Analysis: $C_{22}H_{22}F_4N_2O_7S$ (534.48)
C,49.44; H,4.15; F,14.22; N,5.24; O,20.95; S,6.00:Calcd.
C,49.40; H,4.20; F,14.13; N,5.15; O,—; S,5.91:Found.

(b)

2-[2-[N-(4-Fluoro-2-trifluoromethylphenyl)sulfamoyl]-benzoylimino]diacetic Acid

Under the conditions of Example 2(b), 3.207 g (6 mmol) of the ester produced in Example 39(a) is saponified with 7 ml (14 mmol) of 2N sodium hydroxide solution in 30 ml of dioxane. The mixture is worked up analogously, yielding 2.279 g (79.4% of theory) of the title compound.

Analysis: $C_{18}H_{14}F_4N_2O_7S$ (478.38)
C,45.19; H,2.95; F,15.88; N,5.86; O,23.41; S,6.70:Calcd.
C,45.28; H,3.03; F,15.82; N,5.80; O,—; S,6.59:Found.

EXAMPLE 40

2-[4-[N-(4-Fluoro-3-trifluoromethylphenyl)sulfamoyl]-benzoylimino]diacetic Acid

(a)

2-[4-[N-(4-Fluoro-3-trifluoromethylphenyl)sulfamoyl]-benzoylimino]diacetic Acid Diethyl Ester

Under the conditions of Example 2(a), 3.633 g (10 mmol) of 4-[N-(4-fluoro-3-trifluoromethylphenyl)sulfamoyl]benzoic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.238 g (79.3% of theory)
Analysis: $C_{22}H_{22}F_4N_2O_7S$ (534.48)
C,49.44; H,4.15; F,14.22; N,5.24; O,20.95; S,6.00:Calcd.
C,49.40; H,4.21; F,14.12; N,5.26; O,—; S,5.89:Found.

(b)

2-[4-[N-(4-Fluoro-3-trifluoromethylphenyl)sulfamoyl]-benzoylimino]diacetic Acid

Under the conditions of Example 2(b), 3.10 g (5.8 mmol) of the ester produced in Example 40(a) is saponified with 7 ml (14 mmol) of 2N sodium hydroxide solution in 30 ml of dioxane. The mixture is worked up analogously, yielding 2.203 g (79.4% of theory) of the title compound.

Analysis: $C_{18}H_{14}F_4N_2O_7S$ (478.38)
C,45.19; H,2.95; F,15.88; N,5.86; O,23.41; S,6.70:Calcd.
C,45.27; H,3.02; F,15.79; N,5.90; O,—; S,6.73:Found.

EXAMPLE 41

2-[4-[N-(4-Fluoro-2-trifluoromethylphenyl)sulfamoyl]-benzoylimino]diacetic Acid

(a)

2-[4-[N-(4-Fluoro-2-trifluoromethylphenyl)sulfamoyl]-benzoylimino]diacetic Acid Diethyl Ester

Under the conditions of Example 2(a), 3.633 g (10 mmol) of 4-[N-(4-fluoro-2-trifluoromethylphenyl)sulfamoyl]benzoic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.217 g (78.9% of theory)
Analysis: $C_{22}H_{22}F_4N_2O_7S$ (534.48)
C,49.44; H,4.15; F,14.22; N,5.24; O,20.95; S,6.00:Calcd.
C,49.52; H,4.21; F,14.16; N,5.28; O,—; S,5.89:Found.

(b)

2-[4-[N-(4-Fluoro-2-trifluoromethylphenyl)sulfamoyl]-benzoylimino]diacetic Acid

Under the conditions of Example 2(b), 2.672 g (5 mmol) of the ester prepared in Example 41(a) is saponified with 6 ml (12 mmol) of 2N sodium hydroxide solution in 25 ml of dioxane. The mixture is worked up analogously, yielding 1.875 g (78.4% of theory) of the title compound.

Analysis: $C_{18}H_{14}F_4N_2O_7S$ (478.38)
C,45.19; H,2.95; F,15.88; N,5.86; O,23.41; S,6.70:Calcd.
C,45.28; H,3.02; F,15.80; N,5.91; O,—; S,6.74:Found.

EXAMPLE 42

2-[2-[N-(4-Fluoro-3-trifluoromethylphenyl)sulfamoyl]-benzoylimino]diacetic Acid

(a)

2-[2-[N-(4-Fluoro-3-trifluoromethylphenyl)sulfamoyl]-benzoylimino]diacetic Acid Diethyl Ester

Under the conditions of Example 2(a), 3.633 g (10 mmol) of 2-[N-(4-fluoro-3-trifluoromethylphenyl)sulfamoyl]benzoic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is chromatographed on silica gel. The title compound is eluted with ethyl acetate.

Yield: 4.287 g (80.2% of theory)
Analysis: $C_{22}H_{22}F_4N_2O_7S$ (534.48)
C,49.44; H,4.15; F,14.22; N,5.24; O,20.95; S,6.00:Calcd.
C,49.36; H,4.22; F,14.09; N,5.31; O,—; S,5.89:Found.

(b)

2-[2-[N-(4-Fluoro-3-trifluoromethylphenyl)sulfamoyl]-benzoylimino]diacetic Acid

Under the conditions of Example 2(b), 3.26 g (6.1 mmol) of the ester produced in Example 42(a) is saponified with 7 ml (14 mmol) of 2N sodium hydroxide solution in 25 ml of dioxane. The mixture is worked up analogously, yielding 2.285 g (78.3% of theory) of the title compound.

Analysis: $C_{18}H_{14}F_4N_2O_7S$ (478.38)
C,45.19; H,2.95; F,15.88; N,5.86; O,23.41; S,6.70:Calcd.
C,45.30; H,3.04; F,15.79; N,5.82; O,—; S,6.73:Found.

EXAMPLE 43

2-[3-[N-(4-Fluoro-2-trifluoromethylphenyl)sulfamoyl]-propionylamino]acetic Acid (a)

2-[3-[N-(4-Fluoro-2-trifluoromethylphenyl)sulfamoyl]-propionylamino]acetic Acid Ethyl Ester Under the conditions of Example 2(a), 3.152 g (10 mmol) of 3-[N-(4-fluoro-2-trifluoromethylphenyl)sulfamoyl]propionic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.179 g (79.4% of theory)
Analysis: $C_{14}H_{16}F_4N_2O_5S$ (400.35)
C,42.00; H,4.03; F,18.98; N,7.00; O,19.98; S,8.01:Calcd.
C,41.93; H,4.11; F,18.91; N,7.10; O,—; S,7.89:Found.

(b)

2-[3-[N-(4-Fluoro-2-trifluoromethylphenyl)sulfamoyl]-propionylamino]acetic Acid

Under the conditions of Example 2(b), 3.203 g (8 mmol) of the ester prepared in Example 43(a) is saponified with 9 ml (18 mmol) of 2N sodium hydroxide solution in 35 ml of dioxane. The mixture is worked up in analogy to Example 2(b), producing 2.41 g (80.9% of theory) of the title compound.

Analysis: $C_{12}H_{12}F_4N_2O_5S$ (372.30)
C,38.71; H,3.25; F,20.41; N,7.52; O,21.49; S,8.61:Calcd.
C,38.78; H,3.30; F,20.35; N,7.60; O,—; S,8.58:Found.

EXAMPLE 44

2-[3-[N-(4-Fluoro-2-trifluoromethylphenyl)sulfamoyl]-propionylamino]-2-methylacetic Acid (a)

2-[3-[N-(4-Fluoro-2-trifluoromethylphenyl)sulfamoyl]-propionylamino]-2-methylacetic Acid Ethyl Ester Under the conditions of Example 2(a), 3.152 g (10 mmol) of 3-[N-(4-fluoro-2-trifluoromethylphenyl)sulfamoyl]propionic acid, 1.536 g (10 mmol) of L-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.245 g (78.3% of theory)
Analysis: $C_{15}H_{18}F_4N_2O_5S$ (414.37)
C,43.48; H,4.38; F,18.34; N,6.76; O,19.31; S,7.74:Calcd.
C,43.51; H,4.46; F,18.30; N,6.82; O,—; S,7.67:Found.

(b)

2-[3-[N-(4-Fluoro-2-trifluoromethylphenyl)sulfamoyl]-propionylamino]-2-methylacetic Acid Under the conditions of Example 2(b), 3.108 g (7.5 mmol) of the ester produced in Example 44(a) is saponified with 9 ml (18 mmol) of 2N sodium hydroxide solution in 35 ml of dioxane. The mixture is worked up in analogy to Example 2(b), thus producing 2.24 g (77.3% of theory) of the title compound.

Analysis: $C_{13}H_{14}F_4N_2O_5S$ (386.32)
C,40.42; H,3.65; F,19.67; N,7.25; O,20.71; S,8.30:Calcd.
C,40.45; H,3.70; F,19.62; N,7.31; O,—; S,8.24:Found.

EXAMPLE 45

2-[3-[N-(4-Fluoro-2-trifluoromethylphenyl)sulfamoyl]-propionylamino]-2-hydroxymethylacetic Acid (a)

2-[3-[N-(4-Fluoro-2-trifluoromethylphenyl)sulfamoyl]-propionylamino]-2-hydroxymethylacetic Acid Methyl Ester Under the conditions of Example 2(a), 3.152 g (10 mmol) of 3-[N-(4-fluoro-2-trifluoromethylphenyl)sulfamoyl]propionic acid, 1.556 g (10 mmol) of L-serine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.372 g (81.0% of theory)
Analysis: $C_{14}H_{16}F_4N_2O_6S$ (416.35)
C,40.39; H,3.87; F,18.25; N,6.73; O,23.06; S,7.70:Calcd.
C,40.30; H,4.01; F,18.20; N,6.67; O,—; S,7.63:Found.

(b)

2-[3-[N-(4-Fluoro-2-trifluoromethylphenyl)sulfamoyl]-propionylamino]-2-hydroxymethylacetic Acid Under the conditions of Example 4(b), 2.498 g (6 mmol) of the ester prepared in Example 45(a) is saponified with 7 ml (14 mmol) of 2N barium hydroxide solution in 25 ml of dioxane. The mixture is worked up analogously to Example 4(b), thus obtaining 1.912 g (79.2% of theory) of the title compound.

Analysis: $C_{13}H_{14}F_4N_2O_6S$ (402.32)
C,38.81; H,3.51; F,18.89; N,6.96; O,23.86; S,7.97:Calcd.
C,38.90; H,3.59; F,18.92; N,7.02; O,—; S,7.93:Found.

EXAMPLE 46

2-[3-[N-(4-Fluoro-2-trifluoromethylphenyl)sulfamoyl]-propionylamino]-2-(1-hydroxyethyl)acetic Acid (a)

2-[3-[N-(4-Fluoro-2-trifluoromethylphenyl)sulfamoyl]-propionylamino]-2-(1-hydroxyethyl)acetic Acid Ethyl Ester Under the conditions of Example 2(a), 3.152 g (10 mmol) of 3-[N-(4-fluoro-2-trifluoromethylphenyl)sulfamoyl]propionic acid, 1.736 g (10 mmol) of L-threonine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.484 g (78.4% of theory)
Analysis: $C_{16}H_{20}F_4N_2O_6S$ (444.40)
C,43.24; H,4.54; F,17.10; N,6.30; O,21.60; S,7.22:Calcd.
C,43.16; H,4.59; F,17.04; N,6.35; O,—; S,7.26:Found.

(b)

2-[3-[N-(4-Fluoro-2-trifluoromethylphenyl)sulfamoyl]-propionylamino]-2-(1-hydroxyethyl)acetic Acid Under the conditions of Example 4(b), 2.666 g (6 mmol) of the ester produced in Example 46(a) is saponified with 6.5 ml (13 mmol) of 2N barium hydroxide solution in 30 ml of dioxane. The mixture is worked up analogously to Example 4(b), thus obtaining 1.871 g (74.9% of theory) of the title compound.

Analysis: $C_{14}H_{16}F_4N_2O_6S$ (416.35)
C,40.39; H,3.87; F,18.25; N,6.73; O,23.06; S,7.70:Calcd.
C,40.29; H,3.83; F,18.18; N,6.66; O,—; S,7.61:Found.

EXAMPLE 47

3-[3-[N-(4-Fluoro-2-trifluoromethylphenyl)sulfamoyl]-propionylamino]-3-carboxypropionic Acid (a)

3-[3-[N-(4-Fluoro-2-trifluoromethylphenyl)sulfamoyl]-propionylamino]-3-methoxycarbonylpropionic Acid Methyl Ester Under the conditions of Example 2(a), 3.152 g (10 mmol) of 3-[N-(4-fluoro-2-trifluoromethylphenyl)sulfamoyl]propionic acid, 1.836 g (10 mmol) of L-aspartic acid dimethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.557 g (77.6% of theory)
Analysis: $C_{16}H_{18}F_4N_2O_7S$ (458.38)
C,41.93; H,3.96; F,16.58; N,6.11; O,24.43; S,7.00:Calcd.
C,41.98; H,4.03; F,16.62; N,6.08; O,—; S,6.94:Found.

(b)

3-[3-[N-(4-Fluoro-2-trifluoromethylphenyl)sulfamoyl]-propionylamino]-3-carboxypropionic Acid Under the conditions of Example 2(b), 2.750 g (6 mmol) of the ester prepared in Example 47(a) is saponified with 7 ml (14 mmol) of 2N sodium hydroxide solution in 25 ml of dioxane. The mixture is worked up analogously to Example 2(b), thus obtaining 2.102 g (81.4% of theory) of the title compound.

Analysis: $C_{14}H_{14}F_4N_2O_7S$ (430.33)
C,39.08; H,3.28; F,17.66; N,6.51; O,26.03; S,7.45:Calcd.
C,39.00; H,3.35; F,17.61; N,6.58; O,—; S,7.50:Found.

EXAMPLE 48

3-[3-[N-(4-Fluoro-2-trifluoromethylphenyl)sulfamoyl]-propionylamino]propionic Acid (a)

3-[3-[N-(4-Fluoro-2-trifluoromethylphenyl)sulfamoyl]-propionylamino]propionic Acid Ethyl Ester Under the conditions of Example 2(a), 3.152 g (10 mmol) of 3-[N-(4-fluoro-2-trifluoromethylphenyl)sulfamoyl]propionic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.282 g (79.2% of theory)
Analysis: $C_{15}H_{18}F_4N_2O_5S$ (414.37)
C,43.48; H,4.38; F,18.34; N,6.76; O,19.31; S,7.74:Calcd.
C,43.44; H,4.47; F,18.38; N,6.70; O,—; S,7.69:Found.

(b)

3-[3-[N-(4-Fluoro-2-trifluoromethylphenyl)sulfamoyl]-propionylamino]propionic Acid Under the conditions of Example 2(b), 2.196 g (5.3 mmol) of the ester produced in Example 48(a) is saponified with 6 ml (12 mmol) of 2N sodium hydroxide solution in 25 ml of dioxane and worked up analogously to Example 2(b), yielding 1.609 g (78.6% of theory) of the title compound.

Analysis: $C_{13}H_{14}F_4N_2O_5S$ (386.32)
C,40.42; H,3.65; F,19.67; N,7.25; O,20.71; S,8.30:Calcd.
C,40.40; H,3.71; F,19.70; N,7.20; O,—; S,8.28:Found.
$pK_a$ (37° C.): 6.91 ppm/pH: 5.21 $LD_{50}$ [mmol/kg], mouse: 4

EXAMPLE 49

2-[3-[N-(4-Fluoro-2-trifluoromethylphenyl)sulfamoyl]-propionylimino]diacetic Acid (a)

3-[3-[N-(4-Fluoro-2-trifluoromethylphenyl)sulfamoyl]-propionylimino]diacetic Acid Diethyl Ester Under the conditions of Example 2(a), 3.152 g (10 mmol) of 3-[N-(4-fluoro-2-trifluoromethylphenyl)sulfamoyl]propionic acid, 2.257 g (10 mmol) of iminodiacetic acid diethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.741 g (76.9% of theory)
Analysis: $C_{18}H_{22}F_4N_2O_7S$ (486.44)
C,44.45; H,4.56; F,15.62; N,5.76; O,23.02; S,6.59:Calcd.
C,44.39; H,4.51; F,15.56; N,5.71; O,—; S,6.52:Found.

(b)

2-[3-[N-(4-Fluoro-2-trifluoromethylphenyl)sulfamoyl]-propionylamino]diacetic Acid Under the conditions of Example 2(b), 2.432 g (5 mmol) of the ester produced in Example 49(a) is saponified with 8 ml (16 mmol) of 2N sodium hydroxide solution in 30 ml of dioxane and worked up analogously to Example 2(b), thus obtaining 1.683 g (78.2% of theory) of the title compound.

Analysis: $C_{14}H_{14}F_4N_2O_7S$ (430.33)

C,39.08; H,3.28; F,17.66; N,6.51; O,26.03; S,7.45:Calcd.

C,39.02; H,3.33; F,17.61; N,6.46; O,—; S,7.51:Found.

EXAMPLE 50

2-[4-[N-(4-Fluoro-3-trifluoromethylphenyl)sulfamoylmethyl]benzoylamino]acetic Acid (a)

2-[4-[N-(4-Fluoro-3-trifluoromethylphenyl)sulfamoylmethyl]benzoylamino]acetic Acid Ethyl Ester Under the conditions of Example 2(a), 3.773 g (10 mmol) of 4-[N-(4-fluoro-3-trifluoromethylphenyl)sulfamoylmethyl]benzoic acid, 1.396 g (10 mmol) of glycine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.625 g (78.4% of theory)

Analysis: $C_{19}H_{18}F_4N_2O_5S$ (462.42)

C,49.35; H,3.92; F,16.43; N,6.06; O,17.30; S,6.93:Calcd.

C,49.42; H,3.99; F,16.37; N,6.02; O,—; S,6.88:Found.

(b)

2-[4-[N-(4-Fluoro-3-trifluoromethylphenyl)sulfamoylmethyl]benzoylamino]acetic Acid Under the conditions of Example 2(b), 1.850 g (4 mmol) of the ester produced in Example 50(a) is saponified with 5 ml (10 mmol) of 2N sodium hydroxide solution in 20 ml of dioxane. The mixture is worked up analogously to Example 2(b), yielding 1.395 g (80.3% of theory) of the title compound.

Analysis: $C_{17}H_{14}F_4N_2O_5S$ (434.37)

C,47.01; H,3.25; F,17.49; N,6.45; O,18.42; S,7.38:Calcd.

C,47.07; H,3.29; F,17.42; N,6.48; O,—; S,7.34:Found.

EXAMPLE 51

2-[4-[N-(4-Fluoro-3-trifluoromethylphenyl)sulfamoylmethyl]benzoylamino]-2-hydroxymethylacetic Acid (a)

2-[4-[N-(4-Fluoro-3-trifluoromethylphenyl)sulfamoylmethyl]benzoylamino]-2-hydroxymethylacetic Acid Methyl Ester Under the conditions of Example 2(a), 3.773 g (10 mmol) of 4-[N-(4-fluoro-3-trifluoromethylphenyl)sulfamoylmethyl]benzoic acid, 1.556 g (10 mmol) of L-serine methyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.88 g (81.1% of theory)

Analysis: $C_{19}H_{18}F_4N_2O_6S$ (478.42)

C,47.70; H,3.79; F,15.88; N,5.86; O,20.07; S,6.70:Calcd.

C,47.64; H,3.83; F,15.83; N,5.90; O,—; S,6.65:Found.

(b)

2-[4-[N-(4-Fluoro-3-trifluoromethylphenyl)sulfamoylmethyl]benzoylamino]-2-hydroxymethylacetic Acid Under the conditions of Example 4(b), 3.588 g (7.5 mmol) of the ester prepared in Example 51(a) is saponified with 8 ml (16 mmol) of 2N barium hydroxide solution in 40 ml of dioxane. The mixture is worked up analogously to Example 4(b), thus obtaining 2.731 g (78.4% of theory) of the title compound.

Analysis: $C_{18}H_{16}F_4N_2O_6S$ (464.39)

C,46.56; H,3.47; F,16.36; N,6.03; O,20.07; S,6.90:Calcd.

C,46.51; H,3.44; F,16.32; N,6.08; O,—; S,6.85:Found.

EXAMPLE 52

3-[4-[N-(4-Fluoro-3-trifluoromethylphenyl)sulfamoylmethyl]benzoylamino]propionic Acid (a)

3-[4-[N-(4-Fluoro-3-trifluoromethylphenyl)sulfamoylmethyl]benzoylamino]propionic Acid Ethyl Ester Under the conditions of Example 2(a), 3.773 g (10 mmol) of 4-[N-(4-fluoro-3-trifluoromethylphenyl)sulfamoylmethyl]benzoic acid, 1.536 g (10 mmol) of β-alanine ethyl ester hydrochloride, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is purified by column chromatography on silica gel. The title compound is eluted with ethyl acetate.

Yield: 3.187 g (76.9% of theory)

Analysis: $C_{15}H_{18}F_4N_2O_5S$ (414.37)

C,43.48; H,4.38; F,18.34; N,6.76; O,19.31; S,7.74:Calcd.

C,43.52; H,4.44; F,18.30; N,6.72; O,—; S,7.70:Found.

(b)

3-[4-[N-(4-Fluoro-3-trifluoromethylphenyl)sulfamoylmethyl]benzoylamino]propionic Acid Under the conditions of Example 2(b), 2.486 g (6 mmol) of the ester prepared in Example 52(a) is saponified with 7 ml (14 mmol) of 2N sodium hydroxide solution in 35 ml of dioxane. The product is worked up analogously to Example 2(b), thus obtaining 1.806 g (77.9% of theory) of the title compound.

Analysis: $C_{13}H_{14}F_4N_2O_5S$ (386.32)

C,40.42; H,3.65; F,19.67; N,7.25; O,20.71; S,8.30:Calcd.

C,40.38; H,3.66; F,19.60; N,7.22; O,—; S,8.27:Found.

EXAMPLE 53

2-[2-[N-(4-Fluoro-2-trifluoromethylphenyl)sulfamoyl]acetylamino]ethanesulfonic Acid Under the conditions of Example 2(a), 3.012 g (10 mmol) of 2-[N-(4-fluoro-2-trifluoromethylphenyl)sulfamoyl]acetic acid, 1.252 g (10 mmol) of 2aminoethanesulfonic acid, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is dissolved in distilled water, extracted with ethyl acetate, and converted into the free acid by treatment with acidic cation exchanger. The title compound is obtained by freeze-drying the aqueous solution.

Yield: 2.952 g (72.3% of theory)
Analysis: $C_{11}H_{12}F_4N_2O_6S_2$ (408.35)
C,32.36; H,2.96; F,18.61; N,6.86; O,23.51; S,15.70:Calcd.
C,32.28; H,3.04; F,18.55; N,6.82; O,—; S,15.68:Found.

EXAMPLE 54

4-[2-[N-(4-Fluoro-2-trifluoromethylphenyl)sulfamoyl]acetylamino]benzenesulfonic Acid Under the conditions of Example 2(a), 3.012 g (10 mmol) of 2-[N-(4-fluoro-2-trifluoromethylphenyl)sulfamoyl]acetic acid, 1.732 g (10 mmol) of 4-aminobenzenesulfonic acid, 1.531 g (10 mmol) of hydroxybenzotriazole, hydrate, as well as 1.012 g (10 mmol) of triethylamine and 2.063 g (10 mmol) of dicyclohexylcarbodiimide are reacted and worked up analogously. The crude product is dissolved in distilled water, extracted with ethyl acetate, and converted into the free acid by treatment with acidic cation exchanger, thus obtaining the title compound by freeze-drying of the aqueous solution.

Yield: 3.706 g (81.2% of theory)
Analysis: $C_{15}H_{12}F_4N_2O_6S_2$ (456.39)
C,39.48; H,2.65; F,16.65; N,6.14; O,21.03; S,14.05:Calcd.
C,39.52; H,2.72; F,16.60; N,6.18; O,—; S,14.00:Found.

EXAMPLE 55

2-[2-[N-(4-Fluoro-2-trifluoromethylphenyl)sulfamoyl]acetylimino]diacetic Acid
Mono-(N-methyl-N2,3-dihydroxypropyl)amide In 120 ml of dimethylformamide, 4.163 g (10 mmol) of the diacetic acid prepared in Example 10(b) is stirred with 2.476 g (12 mmol) of dicyclohexylcarbodiimide overnight at room temperature. Then, under agitation, 2.103 g (20 mmol) of N-methyl-2,3-dihydroxypropylamine in 20 ml of dimethylformamide is added dropwise thereto, and the mixture is stirred for 5 hours, concentrated to dryness, taken up in distilled water, and filtered off from the urea. The solution is extracted with ethyl acetate. By adding cation exchanger in the H+ form, the acid is liberated from the salt. The product is filtered off from the exchanger, thus obtaining the title compound by freeze-drying of the aqueous solution.

Yield: 4.239 g (84.2% of theory)
Analysis: $C_{17}H_{21}F_4N_3O_8S$ (503.45)
C,40.56; H,4.21; F,15.09; N,8.35; O,25.42; S,6.37:Calcd.
C,40.50; H,4.28; F,15.12; N,8.41; O,—; S,6.31:Found.

EXAMPLE 56

Preparation of a Solution of
2-[2-[N-(4-Fluoro-3-trifluoromethylphenyl)sulfamoyl]acetylamino]acetic Acid 179.13 g (0.5 mol) of the compound described in Example 2(b) is introduced into 500 ml of water p.i. By adding 5-normal sodium hydroxide solution, a solution is produced which is subsequently adjusted to pH 7.2 with 0.1-normal sodium hydroxide solution. After adding 100 mg of CaNa2 EDTA, the volume is filled up with water p.i. to 1000 ml. The solution is filtered under sterile conditions and dispensed into multivials and/or ampoules.

EXAMPLE 57

Preparation of a Solution of
2-[2-[N-(4-Fluoro-2-trifluoromethylphenyl)sulfamoyl]acetylamino]ethanesulfonic Acid 204.18 g (0.5 mol) of the compound disclosed in Example 53 is introduced into 500 ml of water p.i. By adding 5-normal sodium hydroxide solution, a solution is prepared which is then adjusted to pH 7.2 with 0.1-normal sodium hydroxide solution. After adding 100 mg of CaNa2 EDTA, the volume is filled up to 1000 ml with water p.i. The solution is filtered in the sterile state and dispensed into multivials and/or ampoules.

Production of the Starting Compounds

3-[N-(4-Fluoro-2-trifluoromethylphenyl)sulfamoyl]propionic Acid (a)

3-[N-(4-Fluoro-2-trifluoromethylphenyl)sulfamoyl]propionic Acid Methyl Ester 8.96 g (50 mmol) of 4-fluoro-2-trifluoromethylaniline is dissolved in 100 ml of pyridine and under cold conditions combined under stirring with 9.52 g (50 mmol) of 3-chlorosulfonylpropionic acid methyl ester (98.5%). The mixture is agitated for 20 minutes, heated for 4 hours to 40° C., and the pyridine is exhausted under vacuum. The residue is distributed between dichloroethane and 4N hydrochloric acid. The organic solution is washed with water, dried over sodium sulfate, and concentrated to dryness under vacuum. The residue is purified by column chromatrography on silica gel. The title compound is eluted with ethyl acetate.

Yield: 11.920 g (72.4% of theory)
Analysis: $C_{11}H_{11}F_4NO_4S$ (329.27)
C,40.13; H,3.37; F,23.08; N,4.25; O,19.44; S,9.74:Calcd.
C,40.22; H,3.44; F,23.03; N,4.21; O,—; S,9.70:Found.

(b)

3-[N-(4-Fluoro-2-trifluoromethylphenyl)sulfamoyl]propionic Acid 3.293 g (10 mmol) of the ester prepared in (a) is dissolved in 50 ml of dioxane and combined with 10 ml (20 mmol) of 2N sodium hydroxide solution. The mixture is stirred at 50° C. until no starting material can be detected any longer. The solution is set to a pH of 4 with hydrochloric acid and concentrated to dryness under vacuum. The residue is distributed between dichloromethane and acidified water. The organic solution is washed with water, dried over sodium sulfate, and concentrated to dryness under vacuum, thus obtaining 2.572 g (81.6% of theory) of the title compound.

Analysis: $C_{10}H_9F_4NO_4S$ (315.24)
C,38.10; H,2.88; F,24.11; N,4.44; O,20.30; S,10.17:Calcd.
C,38.15; H,2.95; F,24.03; N,4.48; O,—; S,10.09:Found.

2-[N-(4-Fluoro-2-trifluoromethylphenyl)sulfamoyl]benzoic Acid Methyl Ester 250 ml of dichloromethane is combined with 9.38 g (52.37 mmol) of 4-fluoro-2-trifluoromethylaniline and 6 ml (14.3 mmol) of pyridine. The mixture is cooled with ice water and under agitation and exclusion of moisture, 13.52 g (57.62 mmol) of 2-chlorosulfonylbenzoic acid methyl ester is added in small increments. The mixture is agitated overnight, washed with 2N hydrochloric acid and water, the dichloromethane solution is dried over sodium sulfate and concentrated to dryness under vacuum. The residue is crystallized from ethyl acetate/hexane. The title compound melts at 143°-145° C.

Yield: 10.28 g (52.0% of theory)

2-[N-(4-Fluoro-2-trifluoromethylphenyl)sulfamoyl]benzoic Acid 6,25 g (16.56 mmol) of 2-[N-(4-fluoro-2-trifluoromethylphenyl)sulfamoyl]benzoic acid methyl ester is dissolved in 60 ml of dioxane and combined with 25 ml (50 mmol) of 2N sodium hydroxide solution. The mixture is heated on a water bath until all of the starting material has disappeared. The solution is then concentrated to dryness under vacuum, combined with 2N hydrochloric acid, and the thus-precipitated material is dissolved in ethyl acetate. The organic solution is dried over sodium sulfate, concentrated to dryness, and the residue is crystallized from ethyl acetate/hexane. The title compound melts at 148° C.

Yield: 5.45 g (90.5% of theory)

2-[N-(4-Fluoro-2-trifluoromethylphenyl)sulfamoyl]benzoic Acid Methyl Ester 9.05 g (50 mmol) of 4-fluoro-3-trifluoromethylaniline (99%) and 5 ml (62 mmol) of pyridine are dissolved in 150 ml of dichloromethane. The mixture is cooled to −5° C. and then, with agitation and exclusion of moisture, 13.03 g (50 mmol) of 2-chlorosulfonylbenzoic acid methyl ester (90%) is added in small increments. The mixture is agitated for 2 days at room temperature, washed with 2N hydrochloric acid and water, the dichloromethane solution is dried over sodium sulfate and concentrated to dryness under vacuum. The residue is crystallized from ethyl acetate/hexane. The title compounds melts at 99°-101° C.

Yield: 12.093 g (64.1% of theory)

2-[N-(4-Fluoro-3-trifluoromethylphenyl)sulfamoyl]benzoic Acid 10.37 g (27.5 mmol) of 2-[N-(4-Fluoro-2-trifluoromethylphenyl)sulfamoyl]benzoic acid methyl ester is dissolved in 70 ml of dioxane and saponified, as described in the preceding example, with 40 ml (80 mmol) of 2N sodium hydroxide solution. The mixture is worked up analogously, thus obtaining the title compound after crystallization from ethyl acetate/hexane, melting point 164-°166° C.

Yield: 9.32 g (93.3% of theory)

4-[N-(4-Fluoro-3-trifluoromethylphenyl)sulfamoyl]benzoic Acid 10 g (55.8 mmol) of 4-fluoro-3-trifluoromethylaniline and 6 ml (74.3 mmol) of pyridine are dissolved in 250 ml of dichloromethane. The mixture is cooled with ice water and, under agitation and exclusion of moisture, 12.7 g (57.6 mmol) of 4-chlorosulfonylbenzoic acid is added in incremental portions. The mixture is stirred overnight; the slurry is combined with 75 ml of 2N sodium hydroxide solution, and the organic phase is separated. The alkaline solution is washed with dichloromethane and then adjusted to pH 2 with hydrochloric acid. The product is taken up in ethyl acetate. The solution is washed with water, dried over sodium sulfate and concentrated to dryness. The title compounds melts at 243-°245° C. after crystallization from ethanol.

Yield: 15.54 g (76.7% of theory)

2-[N-(4-Fluoro-3-trifluoromethylphenyl)sulfamoyl]acetic Acid Methyl Ester 13.02 g (72.70 mmol) of 4-fluoro-3-trifluoromethylaniline and 6.79 ml (84.12 mmol) of pyridine are dissolved in 350 ml of dichloromethane. The mixture is cooled to 0° C. and then, under agitation and exclusion of moisture, 13.2 g (72.70 mmol) of 2-chlorosulfonylacetic acid methyl ester (95.3%), dissolved in 50 ml of dichloromethane, is added dropwise thereto. After agitation overnight, the mixture is washed with 2N hydrochloric acid and water. The dichloromethane solution is dried over sodium sulfate, concentrated to dryness under vacuum, and the residue is crystallized from diethyl ether/hexane. The title compound melts at 111-°113° C.

Yield: 19.86 g (86.7% of theory)

2-[N-(4-Fluoro-3-trifluoromethylphenyl)sulfamoyl]acetic Acid 12.79 g (40.57 mmol) of 2-[N-(4-fluoro-3-trifluoromethylphenyl)sulfamoyl]acetic acid methyl ester is dissolved in 110 ml of dioxane and combined with 59 ml (118 mmol) of 2N sodium hydroxide solution. The mixture heated up slightly, and the starting material had disappeared after 15 minutes. The mixture is concentrated to dryness under vacuum, the residue is combined with 2N hydrochloric acid, and the thus-precipitated acid is taken up in ethyl acetate. The organic solution is washed with water, dried over sodium sulfate, and concentrated to dryness under vacuum. The residue is crystallized from ethyl acetate/hexane. The title compound melts at 138°-140° C.

Yield: 11.17 g (91.4% of theory)

4-[N-(4-Fluoro-2-trifluoromethylphenyl)sulfamoylmethyl)benzoic Acid Methyl Ester 5.29 g (29.5 mmol) of 4-fluoro-2-(trifluoromethyl)aniline and 5 ml of pyridine are dissolved in 200 ml of dichloromethane under exclusion of moisture, and the solution is cooled to 0° C. In incremental portions, 7.5 g (29.5 mmol) of 4-chlorosulfonylmethylbenzoic acid methyl ester is added to this solution, and the mixture is stirred for one hour at 0° C. The reaction solution is washed free of pyridine with 2N hydrochloric acid, extracted twice by shaking with water, the organic phase is dried over sodium sulfate, filtered, and evaporated to dryness. The residue is dried under vacuum.

Yield: 10.27 g (26.24 mmol)=89% of theory

Analysis: $C_{16}H_{13}F_4NO_4S$ MW 391.34:

Calcd.: C,49.11; H,3.35; F,19.42; N,3.58; O,16.35; S,8.19%.

Found: C,49.39; H,3.23; F,19.67; N,3.66; S,8.15%.

4-[N-(4-Fluoro-2-trifluoromethylphenyl)sulfamoylmethyl]benzoic Acid 8.6 g (21.98 mmol) of 4-[N-(4-fluoro-2-trifluoromethylphenyl)sulfamoylmethyl]benzoic acid methyl ester is dissolved or suspended in 150 ml of dioxane. To this solution is added 25 ml (50 mmol) of 2N sodium hydroxide solution, and the mixture is stirred for 15 minutes at 60° C. The solution is then acidified with concentrated hydrochloric acid, the acid being precipitated as a solid. This acid is suctioned off, washed with water, and dissolved in 50 ml of ethyl acetate. This solution is dried over sodium sulfate, filtered, evaporated, and the residue dried under vacuum, yielding 7.35 g (19.48 mmol)=88.62% of theory.

Analysis: $C_{15}H_{11}F_4NO_4S$ MW 377.31:

Calcd.: C,47.75; H,2.94; F,20.14; N,3.71; O,16.96; S,8.5%.

Found: C,47.88; H,3.07; F,20.25; N,3.56; S,8.35%.

2-[N-(4-Fluoro-2-trifluoromethylphenyl)sulfamoyl]acetic Acid Methyl Ester 5 g (27.64 mmol) of 4-fluoro-2-(trifluoromethyl)aniline is dissolved in 25 ml of dry pyridine, and the solution is cooled to 0° C. While maintaining the temperature, a solution of 4.82 g (27.4 mmol) of chlorosulfonylacetic acid methyl ester in 20 ml of dichloromethane is added dropwise to the cooled solution during the course of about 10 minutes. Then the mixture is stirred for 6 hours at room temperature. The reaction solution is then diluted with 100 ml of dichloromethane, the pyridine is extracted by shaking with 2N hydrochloride acid, the organic phase is dried over magnesium sulfate, filtered, and evaporated to dryness. The residue is crystallized from diethyl ether/hexane 1:1, thus obtaining 7.35 g (23.32 mmol)=84.35% of theory of a crystallized product, mp 84°14 86° C.

2-[N-(4-Fluoro-2-trifluoromethylphenyl)sulfamoyl]acetic Acid 2.2 g (6.98 mmol) of 2-[N-(4-fluoro-2-trifluoromethylphenyl)sulfamoyl]acetic acid methyl ester is dissolved in 20 ml of dioxane, and the solution is combined with 10 ml (20 mmol) of 2N sodium hydroxide solution. The mixture heats up slightly, and saponification is completed after 10 minutes. The solution is neutralized with 2N hydrochloric acid under pH control and gently evaporated to dryness under vacuum. The residue is extracted with 30 ml of ethyl acetate, the solution is extracted once by shaking with 10 ml of water, the organic phase is dried over magnesium sulfate, filtered, and evaporated to dryness, thus obtaining 1.96 g (6.51 mmol)=93.2% of theory.

Analysis: $C_9H_7F_4NO_4S$ MW 301.24:

Calcd.: C,35.89; H,2.34; F,25.23; N,4.65; O,21.25; S,10.64%.

Found: C,36.05; H,2.36; F,25.45; N,4.66; S,10.79%.

4-[N-(4-Fluoro-2-trifluoromethylphenyl)sulfamoyl]benzoic Acid 2.21 g (10 mmol) of 4-chlorosulfonylbenzoic acid is suspended under exclusion of moisture in 30 ml of dichloromethane, the suspension is cooled to −5° C. and, at this temperature, a solution of 1.79 g (10 mmol) of 4-fluoro-2-(trifluoromethyl)aniline and 1 ml of pyridine in 20 ml of dichloromethane is added dropwise thereto. After this dropwise addition has been completed, the mixture is allowed to warm up to room temperature and is agitated for another 12 hours. The thus-produced precipitate is suctioned off and extracted with ether. This ether extract and the filtrate are evaporated together, and the residue is dissolved in dichloroethane. The solution is extracted three times with respectively 10 ml of saturated sodium bicarbonate solution. The combined aqueous extracts are acidified with 2N hydrochloric acid and the thus-precipitated product is removed by filtration. The filter residue is dried under vacuum at 50° C., thus obtaining 3.3 g (9.08 mmol)=90.84% of theory.

Analysis: $C_{14}H_9F_4NO_4S$ MW 363.28:

Calcd.: C,46.29; H,2.5; F,20.92; N,3.86; O,17.62; S,8.83%.

Found: C,46.10; H,2.67; F,21.16; N,3.84; S,8.96%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fluorobenzenesulfonamide of formula I

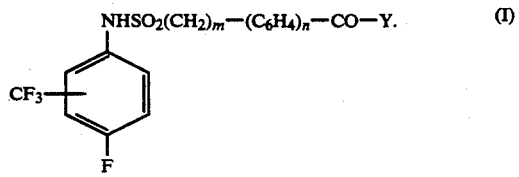

wherein m is the number 0, 1, 2, 3 or 4, n is the number 0 or 1, and

Y is the residue of $C_{1-30}$-aminocarboxylic or aminosulfonic acid, wherein the nitrogen atom forms an amide bond with the carbonyl group of the compound of formula I, the residue has 1-4 acid groups, and the residue has a molecular weight of less than 1000 daltons, with the proviso that m and n are not simultaneously the number 0 and, optionally the acid groups are present in the form of amides or in the form of a salt with organic or inorganic bases.

2. A compound according to claim 1, wherein Y is the residues

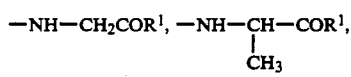

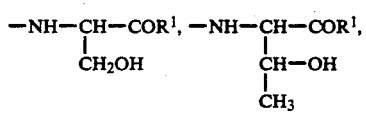

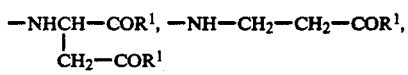

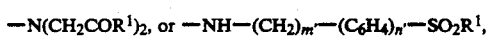

wherein $R^1$ is a hydroxy group or a

residue, wherein $R^2$ and $R^3$, each independently are H, a linear or branched, saturated or unsaturated alkyl group of 1-16 carbon atoms, optionally substituted by 1-5 hydroxy or $C_1$-$C_4$-alkoxy groups, or a $C_{4-6}$-aryl or $C_{7-10}$-aralkyl group, or $R^2$ and $R^3$ jointly with the nitrogen atom are a saturated or unsaturated five- or six-membered ring, optionally containing a further nitrogen, oxygen, sulfur atom or a carbonyl group, and m' n' each independently have the same definitions and m and n.

3. 2-[2-[N-(4-Fluoro-2-trifluoromethylphenyl)sulfamoyl]acetylamino]acetic acid,
2-[2-[N-(4-fluoro-3-trifluoromethylphenyl)sulfamoyl]acetylamino]acetic acid,
2-[2-[N-(4-fluoro-2-trifluoromethylphenyl)sulfamoyl]acetylamino]-2-hydroxymethylacetic acid,
2-[2-[N-(4-fluoro-3-trifluoromethylphenyl)sulfamoyl]acetylamino]-2-hydroxymethylacetic acid,
3-[2-[N-(4-fluoro-2-trifluoromethylphenyl)sulfamoyl]acetylamino]-3-carboxypropionic acid,
3-[2-[N-(4-fluoro-3-trifluoromethylphenyl)sulfamoyl]acetylamino]-3-carboxypropionic acid,
2-[4-[N-(4-fluoro-2-trifluoromethylphenyl)sulfamoyl]benzoylamino]acetic acid,
2-[4-[N-(4-fluoro-3-trifluoromethylphenyl)sulfamoyl]benzoylamino]acetic acid,
2-[4-[N-(4-fluoro-2-trifluoromethylphenyl)sulfamoyl]benzoylamino]-2-hydroxymethylacetic acid,
2-[4-[N-(4-fluoro-3-trifluoromethylphenyl)sulfamoyl]benzoylamino]-2-hydroxymethylacetic acid,
3-[4-[N-(4-fluoro-2-trifluoromethylphenyl)sulfamoyl]benzoylamino]-3-carboxypropionic acid,
3-[4-[N-(4-fluoro-3-trifluoromethylphenyl)sulfamoyl]benzoylamino]-3-carboxypropionic acid,
2-[2-[N-(4-fluoro-2-trifluoromethylphenyl)sulfamoyl]benzoylamino]acetic acid,
2-[2-[N-(4-fluoro-3-trifluoromethylphenyl)sulfamoyl]benzoylamino]acetic acid,
2-[2-[N-(4-fluoro-2-trifluoromethylphenyl)sulfamoyl]benzoylamino]-2-hydroxymethylacetic acid,
2-[2-[N-(4-fluoro-3-trifluoromethylphenyl)sulfamoyl]benzoylamino]-2-hydroxymethylacetic acid,
3-[2-[N-(4-fluoro-2-trifluoromethylphenyl)sulfamoyl]benzoylamino]-3-carboxypropionic acid,
3-[2-[N-(4-fluoro-3-trifluoromethylphenyl)sulfamoyl]benzoylamino]-3-carboxypropionic acid, each a compound of claim 1.

4. A compound of claim 1, wherein m is 1 and n is 0.

5. A compound of claim 1, wherein m is 0 and n is 1.

6. A compound of claim 1, wherein Y is an aminocarboxylic acid.

7. A compound of claim 6, wherein Y is acetylamino.

8. A compound of claim 6, wherein Y is 3-carboxypropionyl-amino.

9. A compound of claim 6, wherein Y is 2-hydroxymethylacetylamino.

10. A compound of claim 1 wherein the $CF_3$ group is in the 2-position.

11. A compound of claim 1 wherein the $CF_3$ group is in the 3-position.

12. A compound of claim 1 wherein Y is an aminosulfonic acid.

13. A compound of claim 1 wherein Y contains two carboxylic acid groups.

14. A compound of claim 1 wherein one or more F atoms are $^{18}F$.

15. A pharmaceutical composition comprising a compound of claim 1 and a pharmaceutically acceptable excipient.

* * * * *